US008026109B2

(12) United States Patent
Ennifar et al.

(10) Patent No.: US 8,026,109 B2
(45) Date of Patent: *Sep. 27, 2011

(54) HAPTEN-CARRIER CONJUGATES FOR TREATING AND PREVENTING NICOTINE ADDICTION

(75) Inventors: Sofiane Ennifar, Silver Spring, MD (US); Ali Ibrahim Fattom, Rockville, MD (US); Robert B. Naso, Gaithersburg, MD (US)

(73) Assignee: Nabi Biopharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/836,165

(22) Filed: Jul. 14, 2010

(65) Prior Publication Data

US 2011/0002957 A1    Jan. 6, 2011

Related U.S. Application Data

(60) Continuation of application No. 11/780,742, filed on Jul. 20, 2007, now Pat. No. 7,776,620, which is a division of application No. 10/909,841, filed on Aug. 3, 2004, now Pat. No. 7,247,502, which is a continuation of application No. 10/330,676, filed on Dec. 30, 2002, now Pat. No. 6,773,891, which is a continuation of application No. 09/784,139, filed on Feb. 16, 2001, now Pat. No. 6,518,031, which is a division of application No. 09/201,800, filed on Dec. 1, 1998, now Pat. No. 6,232,082.

(51) Int. Cl.
*G01N 33/532* (2006.01)
*C07K 1/13* (2006.01)
*C07K 1/04* (2006.01)
*A61K 31/465* (2006.01)
*A61K 39/385* (2006.01)

(52) U.S. Cl. ........ 436/544; 530/405; 514/343; 131/270; 424/1.69; 424/193.1

(58) Field of Classification Search .......................... None
See application file for complete search history.

(56) References Cited

U.S. PATENT DOCUMENTS

| | | |
|---|---|---|
| 3,888,866 A | 6/1975 | Leute et al. |
| 4,045,420 A | 8/1977 | Soffer et al. |
| 4,123,431 A | 10/1978 | Soffer et al. |
| 4,235,864 A | 11/1980 | Kaul et al. |
| 4,375,414 A | 3/1983 | Strahilevitz |
| 4,376,825 A | 3/1983 | Rubenstein et al. |
| 4,620,977 A | 11/1986 | Strahilevitz |
| 4,666,837 A | 5/1987 | Harford et al. |
| 4,791,067 A | 12/1988 | Sheiman et al. |
| 4,813,924 A | 3/1989 | Strahilevitz |
| 5,019,384 A | 5/1991 | Gefter et al. |
| 5,037,645 A | 8/1991 | Strahilevitz |
| 5,256,409 A | 10/1993 | Blincko et al. |
| 5,268,276 A | 12/1993 | Holmgren et al. |
| 5,278,176 A | 1/1994 | Lin |
| 5,283,066 A | 2/1994 | Liu et al. |
| 5,290,784 A * | 3/1994 | Qu et al. .................. 514/279 |
| 5,760,184 A | 6/1998 | Swain et al. |
| 5,773,003 A | 6/1998 | Swain et al. |
| 5,876,727 A | 3/1999 | Swain et al. |
| 6,232,082 B1 | 5/2001 | Ennifar et al. |
| 6,518,031 B2 | 2/2003 | Ennifar et al. |
| 7,247,502 B2 * | 7/2007 | Ennifar et al. .................. 436/543 |
| 7,335,516 B2 | 2/2008 | Fitzpatrick et al. |
| 7,776,620 B2 * | 8/2010 | Ennifar et al. .................. 436/544 |

FOREIGN PATENT DOCUMENTS

| | | |
|---|---|---|
| DE | 2 202 441 | 3/1973 |
| DE | 25 48 196 A1 | 4/1977 |
| EP | 0 194 158 A2 | 9/1986 |
| EP | 0 311 383 B1 | 4/1989 |
| EP | 0 363 041 A1 | 4/1990 |
| EP | 0 496 839 B1 | 8/1992 |
| EP | 0 613 899 B1 | 1/2003 |
| SU | 1 123 704 A | 11/1984 |
| WO | WO 92/03163 A1 | 3/1992 |
| WO | WO 93/12111 A1 | 6/1993 |
| WO | WO 93/23070 A1 | 11/1993 |
| WO | WO 93/23076 A1 | 11/1993 |
| WO | WO 95/07992 A2 | 3/1995 |
| WO | WO 95/27786 A1 | 10/1995 |
| WO | WO 96/30049 A2 | 10/1996 |
| WO | WO 98/14216 A2 | 4/1998 |

OTHER PUBLICATIONS

Abad et al., "Comparison of a Monoclonal Antibody-Based Enzyme-Linked Immunosorbent Assay and Gas Chromatography for the Determination of Nicotine in Cigarette Smoke Condensates", *Analytical Chemistry*, vol. 65, No. 32, pp. 3227-3231, Nov. 15, 1993.
Ambre et al., "A Kinetic Model of Benzoylecgonine Disposition After Cocaine Administraiton in Humans", *Journal of Analytical Toxicology*, vol. 15, No. 1, pp. 17-20, Jan./Feb. 1991.
Bagasra et al., A Potential Vaccine for Cocaine Abuse Prophylaxis, *Immunopharmacology*, vol. 23, No. 3, pp. 173-179, May/Jun. 1992.
Bjercke, "Comparison of Monoclonal and Polyclonal Antibodies to Continue in Nonsotopic and Isotopic Immunoassays", *Journal of Immunological Methods*, vol. 96, pp. 239-246, 1987.
Carroll et al., "Chemical Approaches to the Treatment of Cocaine Abuse", *Pharmaceutical News*, vol. 1, No. 2, pp. 11-16, Jun. 1994.
Castonguay et al., "Synthesis of nornicotine analogues to use as haptens for immunoassay", *J. Org. Chem.*, vol. 44., No. 24, pp. 4332-4337, 1979.

(Continued)

*Primary Examiner* — Shafiqul Haq
(74) *Attorney, Agent, or Firm* — Foley & Lardner LLP

(57) ABSTRACT

Novel hapten-carrier conjugates are capable of inducing the production of antibodies, in vivo, that specifically bind to nicotine. These conjugates comprise a nicotine hapten conjugated to an immunogenic carrier protein. The novel conjugates preserve the chirality of nicotine in its native (S)-(−) state, and have good stability properties. The conjugates are useful in formulating vaccines for active immunization, that are used to prevent and treat nicotine addiction. The antibodies raised in response to the nicotine hapten-carrier conjugate are used for passive immunization. These antibodies are administered for prevention and treatment of nicotine addiction.

3 Claims, 7 Drawing Sheets

OTHER PUBLICATIONS

Castro et al., "Nicotine Antibody Production: Comparison of Two Nicotine Conjugates in Different Animal Species", *Biochemical and Biophysical Research Communications*, vol. 67, No. 2, pp. 583-589, Nov. 17, 1975.

Castro et al., "Nicotine Antibodies: Comparison of Ligand Specificities of Antibodies Produced Against Two Nicotine Conjugates", *Eur. J. Biochem.*, pp. 331-340, 1980.

Castro et al., "Semi-Rigid and Flexible Linkages in Antibody Production for Determination of Nicotine", *Biochemical Archives*, vol. 1, No. 4, pp. 205-214, Nov. 1985.

Castro et al., "Nicotine Enzyme Immunoassay", *Research Communications in Chemical Pathology and Pharmacology*, vol. 51, No. 3, pp. 393-404, Mar. 1986.

Fliniaux et al., "Development of an Enzyme Immunoassay for the Determination of Tobacco Alkaloids in Plant Material", *Phytochemical Analysis*, vol. 3, No. 5, pp. 223-226, Sep./Oct. 1992.

Gallacher, "A Potential Vaccine for Cocaine Abuse Prophlaxis?", *Immunopharmacology*, vol. 27, No. 1, pp. 79-81, Jan./Feb. 1994.

Gastro et al., "Characterization of Antibodies to Nicotine", *Biochemical Archives*, vol. 1, No. 3, pp. 173-183, Aug. 1985, M.B.R. Press, Inc. US.

Hieda et al., "Active Immunization Alters the Plasma Nicotine Concentration in Rats", *Immunization and Nicotine Disposition*, vol. 283, No. 3, pp. 1076-1081, May 14, 1997.

Killian et al., "Effects of Passive Immunization Against Morpine on Heroin Self-Adminstration", *Pharmacology Biochemistry & Behavior*, vol. 9, No. 3, pp. 347-352, 1978.

Kovalev et al., "A Method of Synthesizing Barbituric Acid-Immunogen Medium Antigens", *National Committee of the Ussr for Inventions and Discoveries*, pp. 1-4, Mar. 30, 1982.

Kovalev et al., "Diminishment of the Effect of Morphine in Rats Immunized with a Morphine-Protein Conjugated Antigen", *Khim. Farm*, pp. 615-618, 1979.

Landry et al., "Antibody-Catalyzed Degradation of Cocaine", *Science*, vol. 259, pp. 1899-1901, Mar. 26, 1993.

Langone et al., "Nicotine and Its Metabolites. Radioimmunoassays for Nicotine and Cotinine", *Biochemistry*, vol. 12, No. 24, pp. 5025-5030, 1973.

Langone et al., "Radioimmunoassay of Nicotine, Cotinine and Y-(3-PyridyI)-Y-Oxo-N-Methylbutyramide", *Methods in Enzymology*, vol. 84, pp. 628-640, 1982.

Lu et al., "Chemically Unambiguous Peptide Immunogen: Preparation, Orientation and Antigenicty of Purified Peptide Conjugated to the Multiple Antigen Peptide System", *Molecular Immunology*, vol. 28, No. 6, pp. 623-630, Jun. 1991.

Matsushita et al., "Conjugate of Bovine Serum Albumin with Nicotine", *Biochemical and Biophysical Research Communications*, vol. 57, No. 4, pp. 1006-1010, Apr. 23, 1974.

McKenzie et al., "Cholera Toxin B Subunit as a Carrier Protein to Stimulate a Mucosal Immune Response", *Journal of Immunology*, vol. 133, No. 4, pp. 1818-1824, Oct. 1984.

Pentel et al., "Redistribution of Tricyclic Antidepressants in Rates Using a Drug-Specific Monoclonal Antibody: Dose-Response Relationship", *Drug Metabolism and Disposition*, vol. 19, No. 1, pp. 24-28, Jan./Feb. 1991.

Notice of Allowance issued on Apr. 16, 2010 by the Examiner in U.S. Appl. No. 11/780,742 (US 2008/0026000).

Office Action issued on Mar. 23, 2010 by the Examiner in U.S. Appl. No. 11/780,742 (US 2008/0026000).

Office Action issued on Feb. 23, 2010 by the Examiner in U.S. Appl. No. 11/780,742 (US 2008/0026000).

Office Action issued on Mar. 23, 2010 by the Examiner in U.S. Appl. No. 11/780,742 (US 2008/0026000).

Office Action issued on Jan. 28, 2010 by the Examiner in U.S. Appl. No. 11/780,742 (US 2008/0026000).

Office Action issued on Feb. 4, 2009 by the Examiner in U.S. Appl. No. 11/780,742 (US 2008/0026000).

\* cited by examiner

Effect of Passive Immunization of Rats With Antibodies to 3'AMNic-Suc-rEPA on Nicotine Levels in Brain After Multiple Injection of Nicotine Effect of Passive Immunization of Rats With Antibodies to 3'AMNic-Suc-rEPA on Activity Level After Injection of Nicotine

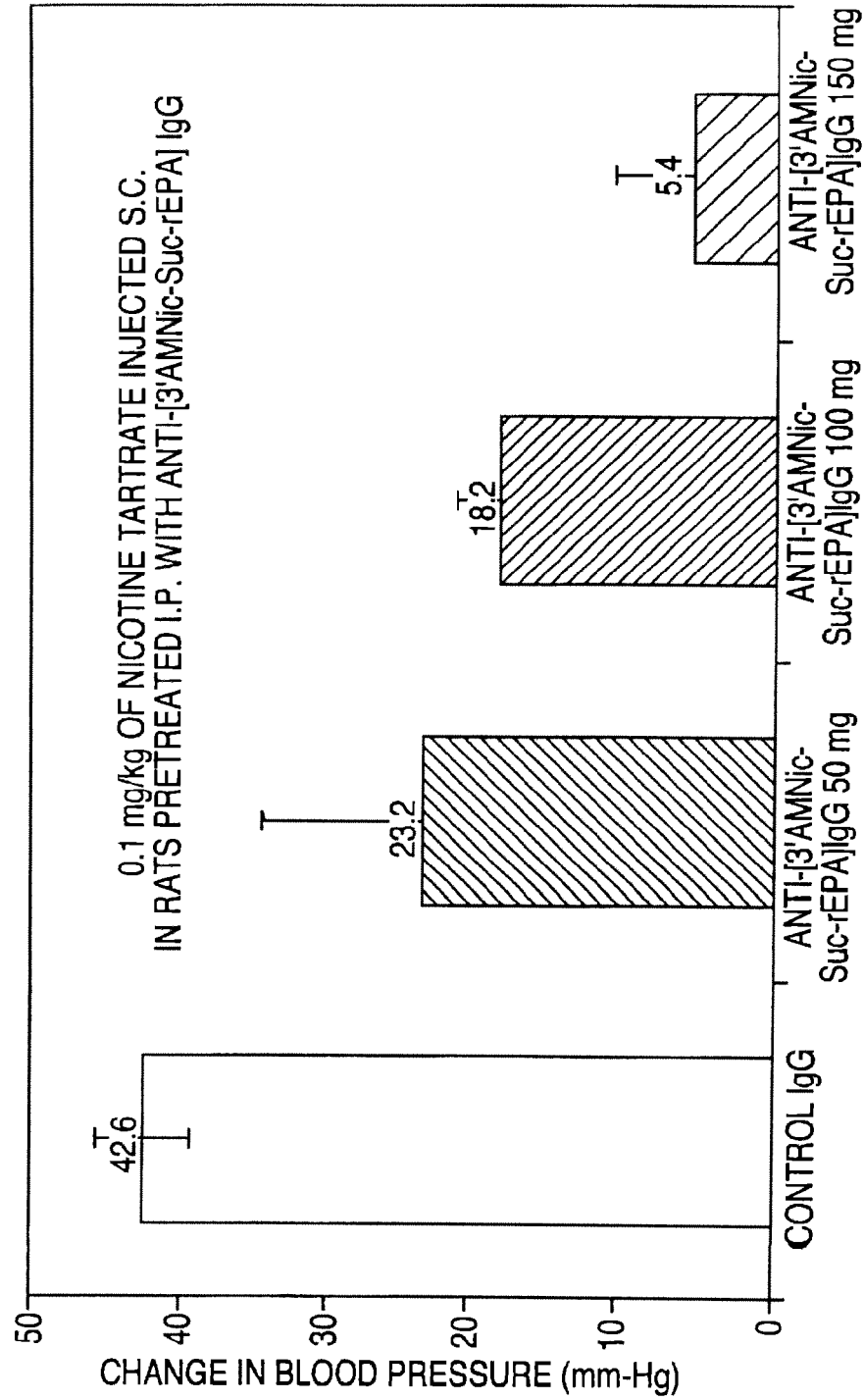

HAPTEN-CARRIER CONJUGATES FOR TREATING AND PREVENTING NICOTINE ADDICTION

FIELD OF THE INVENTION

The present invention relates to treatment and prevention of nicotine addiction. In particular, the invention relates to novel hapten-carrier conjugates which are capable of inducing the production of antibodies. Such antibodies are capable of specifically binding to nicotine. Furthermore, the present invention envisages preventing or treating nicotine addiction by administering a nicotine-carrier conjugate in a pharmaceutically-acceptable formulation. The present invention also contemplates using the antibodies raised in response to the hapten-carrier conjugate for the prevention and treatment of nicotine addiction.

BACKGROUND OF THE INVENTION

Smoking of cigarettes, cigars, and pipes is a prevalent problem in the United States and worldwide. Smoking tobacco and smokeless tobacco are rich in nicotine, which is a known addictive substance. Nicotine is an alkaloid derived from the tobacco plant that is responsible for smoking's psychoactive and addictive effects. Nicotine is formed of two rings linked together by a single bond: an aromatic six-membered ring (pyridine) and an aliphatic five-membered ring (pyrrolidine). The pyrrolidine is N-methylated and linked through its carbon-2 to the carbon-3 of pyridine. Thus, the carbon-2 is chiral, and there is virtually free rotation around the single bond linking the two rings. It has been established that the absolute configuration of carbon-2 is S. Thus, the natural configuration of nicotine is (S)-(−)-nicotine.

Nicotine use is widespread due to the easy availability of cigarettes, cigars, pipes and smokeless tobacco. According to the U.S. Department of Health and Human Services, cigarette smoking is the single leading cause of preventable death in the United States. See also McGinnis et al., *J. Am. Med. Assoc.*, 270, 2207-2211 (1993). Exposure to second hand smoke also has been reported to have serious detrimental health effects, including exacerbation of asthma.

Even though the addictive nature of nicotine is well known, cigarette smoking is prevalent. Peak levels of nicotine in the blood, about 25 to 50 nanograms/ml, are achieved within 10-15 minutes of smoking a cigarette. In humans, smoking a cigarette results in arterial nicotine concentrations being 10-fold higher than venous nicotine concentrations because nicotine is rapidly delivered from the lungs to the heart (see Henningfield (1993) *Drug Alcohol Depend.* 33:23-29). This results in a rapid delivery of high arterial concentrations of nicotine to the brain. Once nicotine crosses the blood-brain barrier, evidence suggests that it binds to cholinergic receptors, which are normally activated by the neurotransmitter acetylcholine, which is involved in respiration, maintenance of heart rate, memory, alertness and muscle movement. When nicotine binds to these receptors, it can affect normal brain function, by triggering the release of other neurotransmitters, such as dopamine. Dopamine is found in the brain in regions involved in emotion, motivation, and feelings of pleasure. It is the release of neurotransmitters, especially dopamine, that is responsible for the tobacco user's addiction to nicotine or other intake of nicotine.

Due to the significant adverse effects of smoking on health, smokers often try to quit. However, the addictive nature of nicotine and the availability of cigarettes add to the continued dependence on nicotine and high failure rate of those who try to quit. Withdrawal symptoms are unpleasant, and are relieved by smoking.

Many therapies for nicotine addiction have been developed, but are largely ineffective. The two most popular therapies remain the nicotine transdermal patch and nicotine incorporated into chewing gum. These therapies, termed "nicotine replacement therapies" (NRT), replace the amount of nicotine which the user previously received from smoking and act to wean the user off nicotine. However, certain drawbacks are seen with this type of therapy. Particularly, there is low penetration of nicotine into the bloodstream and therefore an increased desire to smoke. Problems such as mouth irritation, jaw soreness, nausea, have been associated with use of nicotine chewing gum. Problems such as skin irritations, sleep disturbance, and nervousness have been associated with use of nicotine transdermal patches.

Therefore, an alternative methodology for treating nicotine addiction is needed. The literature recognizes this need and there have been several attempts to provide a methodology for treating nicotine addiction. One of the methods involves the administration of antibodies which have been raised in response to nicotine. However, low molecular weight substances, called haptens, are known to be unable to trigger an immune response in host animals. Nicotine is no exception, and as a small molecule it is not immunogenic. To elicit an antibody response to a hapten, it typically is covalently bound to a carrier protein, and the complex will elicit the production of antibodies that recognize the hapten.

For example, cotinine 4'-carboxylic acid, when bound covalently to keyhole limpet hemocyanin (KLH) was used to generate antibodies to the nicotine metabolite cotinine. Those antibodies were used to determine the presence of cotinine in physiological fluids. See Bjerke et al. *J. Immunol. Methods.*, 96, 239-246 (1987).

Other nicotine antibodies were prepared by Castro et al., (*Eur. J. Biochem.*, 104, 331-340 (1980)). Castro et al., prepared nicotine haptens, conjugated to bovine serum albumin (BSA), with the carrier protein conjugated via a linker at the 6-position of nicotine. Castro et al. prepared additional nicotine conjugates of BSA which were injected into mammals to raise antibodies. In another publication, Castro et al. in *Biochem. Biophys. Res. Commun.* 67, 583-589 (1975) disclose two nicotine albumin conjugates: N-succinyl-6-amino-(±)-nicotine-BSA and 6-(σ-aminocapramido)-(±)-nicotine-BSA. In this 1975 publication, Castro et al. also used antibodies to nicotine carrier conjugate, 6-σ-aminocapramido)-(±)-nicotine-BSA, to determine the levels of nicotine in blood and urine, see *Res. Common Chem. Path. Pharm.* 51, 393-404 (1986).

Swain et al. (WO 98/14216) disclose nicotine carrier conjugates wherein the hapten is conjugated at the 1, 2, 4, 5, 6, or 1' position of the nicotine. Hieda et al., have shown that animals immunized with 6-(carboxymethylureido)-(±)-nicotine, which was linked to keyhole limpet hemocyanin, produced antibodies specific to nicotine. *J. Pharm. and Exper. Thera.* 283, 1076-1081 (1997). Langone et al., prepared the hapten derivative, O-succinyl-3'-hydroxymethyl-nicotine, see *Biochemistry*, 12, 5025-5030, and used the antibodies to this hapten carrier conjugate in radioimmunoassays. See *Methods in Enzymology*, 84, 628-635 (1982). The conjugate produced by Langone is susceptible to hydrolysis. Additionally, Abad et al. in *Anal. Chem.*, 65, 3227-3231 (1993) describe conjugating 3% (hydroxymethyl) nicotine hemisuccinate to bovine serum albumin to produce antibodies to nicotine in order to be able to measure nicotine content in smoke condensate of cigarettes in an ELISA assay.

Therefore, the prior art does not teach a stable nicotine-carrier conjugate that preserves the chiral nature of the nicotine hapten, and that links the hapten to the carrier in a way that conserves the nature of the nicotine epitope(s). Moreover, the art does not teach or suggest methods of preventing and treating nicotine addiction by using such conjugates. Seeman in *Heterocycles*, 22, 165-193, (1984) discloses results of a study of the conformational analysis and chemical reactivity of nicotine.

SUMMARY OF THE INVENTION

In response to the demand for a more effective methodology for treating nicotine addiction, it is one object of the present invention to provide novel nicotine-carrier conjugates that are stable, comprise nicotine in its natural (S)-(−) formation, and employ a nicotine-carrier linkage that preserves the nature of the nicotine epitope(s), and the relative orientation of the two rings of the nicotine molecule. Both rings of nicotine, and their relative orientation, are believed to be essential for the recognition by antibody of nicotine in solution. Such conjugates are capable of stimulating the production of antibodies that are capable of specifically binding to nicotine. Using the inventive conjugates, the inventors have raised serum nicotine levels, and decreased brain nicotine levels, in mammals. Additionally, using the conjugates of the invention, the inventors also have prevented nicotine-induced changes in blood pressure, and locomotor effects.

In another object of the present invention is provided a method of treating nicotine addiction by administering a conjugate of the invention to a patient addicted to nicotine thereby generate anti-nicotine antibodies in that patient. Thus, when the patient smokes (or uses chewing tobacco), the nicotine from these products will be bound by the anti-nicotine antibodies in the blood, preventing the nicotine from crossing the blood-brain barrier, hence eliminating the nicotine-induced alterations in brain chemistry, which is the source of nicotine-addiction. In this regard, it is important that the nicotine-carrier conjugate elicit the production of antibodies that will recognize the native nicotine molecule. As described above, the novel nicotine-carrier conjugates of the invention preserve the chirality and the epitope(s) of naturally-occurring nicotine.

The inventors do not intend to be bound by any particular theory as to how the nicotine conjugates, and the antibodies produced in response to such conjugates, inhibit the effects of nicotine ingested by mammals. In addition to preventing nicotine from crossing the blood brain barrier, the antibodies also may prevent nicotine from binding to other receptors in the peripheral nervous system by simple steric blockage.

These objects can be achieved by providing a hapten-carrier conjugate of formula (I):

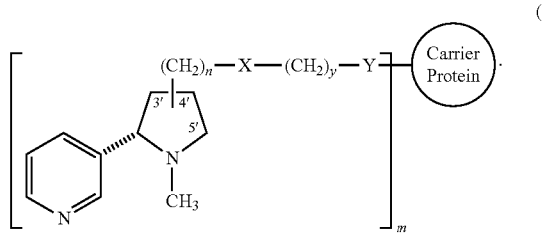

wherein m is 1 to 2500, n is 0 to 12, y is 1 to 12, X is selected from the group consisting of NH—CO, CO—NH, CO—NH—NH, NH—NH—CO, NH—CO—NH, CO—NH—NH—CO, and S—S; Y is selected from the group consisting of NH—CO, CO—NH, CO—NH—NH, NH—NH—CO, NH—CO—NH, CO—NH—NH—CO, and S—S, and the —(CH$_2$)$_n$—X—(CH$_2$)$_y$—Y— moiety is bonded to the 3', 4' or 5' position. In a preferred embodiment of the hapten-carrier conjugate, m is 11 to 17, n is 1, y is 2, X is NH—CO, Y is CO—NH, the carrier protein is exoprotein A and the —(CH$_2$)$_n$—X—(CH$_2$)$_y$—Y— moiety is bonded to the 3' position. In another preferred embodiment of the hapten-carrier conjugate, m is 11 to 17, n is 1, y is 2, X is NH—CO, Y is CO—NH, the carrier protein is exoprotein A and the —(CH$_2$)$_n$—X—(CH$_2$)$_y$—Y— moiety is bonded to the 4' position. In a further preferred embodiment of the hapten-carrier conjugate, m is 11 to 17, n is 1, y is 2, X is NH—CO, Y is CO—NH, the carrier protein is exoprotein A and the —(CH$_2$)$_n$—X—(CH$_2$)$_y$—Y— moiety is bonded to the 5' position. In an additionally preferred embodiment, m is selected from the group consisting of 1 to 20 and 1 to 200.

The above objects also be achieved by providing a hapten-carrier conjugate of formula (III):

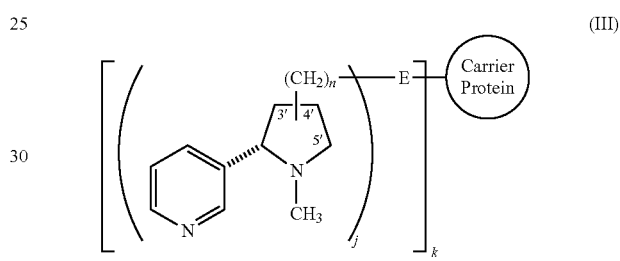

wherein n is 0 to 12, j is 1 to 1000, k is 1 to 20, and E is an amino acid-containing matrix. In a preferred embodiment, the matrix is poly-L-glutamic acid.

The objects can also be achieved by providing an antibody which is produced in response to the hapten-carrier conjugate of Formula (I). In an additional embodiment, the antibody is a functional fragment. In a preferred embodiment, the antibody is a monoclonal antibody. In an additional embodiment of the invention, the antibody is polyclonal.

The objects can also be achieved by providing an antibody which is produced in response to the hapten-carrier conjugate of Formula (III). In an additional embodiment, the antibody is a functional fragment. In a preferred embodiment, the antibody is a monoclonal antibody. In an additional embodiment of the invention, the antibody is polyclonal.

The objects can be achieved by providing a method of treating or preventing nicotine addiction in a patient in need of such treatment comprising administering a therapeutically effective amount of the hapten-carrier conjugate of Formula (I) or (III). Alternatively, the objects can be achieved by providing a method treating or preventing nicotine addiction in a patient in need of such treatment comprising administering a therapeutically effective amount of antibody raised in response to the hapten-carrier conjugates of Formula (I) or (III).

Additionally, the objects can be achieved by providing a vaccine composition which comprises the hapten carrier conjugate of Formula (I) or Formula (III). In addition the vaccine can further comprise an additional therapeutic compound for treating nicotine addiction.

The objects also can be achieved by providing a process for producing an antibody, comprising immunizing a host mammal with a hapten-carrier conjugate of Formula (I) or (III). In a preferred embodiment, the antibody produced is a monoclonal antibody. In an additional embodiment the antibody is polyclonal.

Additional objects can be achieved by providing a kit for determining the presence of nicotine in a sample, comprising an antibody of raised in response to the hapten-carrier conjugate of Formula (I) or Formula (III).

These objects and others apparent to those skilled in the art have been achieved by the invention described below in the detailed description and appended claims.

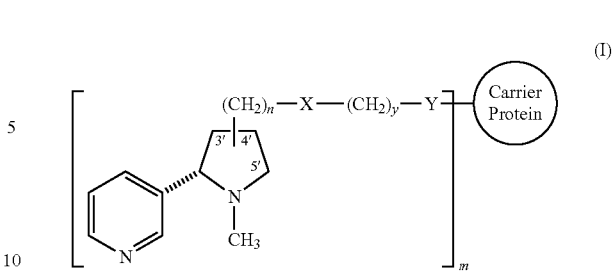

wherein m is 1 to 2,500; n is 0 to 12; y is 1 to 12; X is selected from the group consisting of NH—CO, CO—NH, CO—NH—NH, NH—NH—CO, NH—CO—NH, CO—NH—NH—CO and S—S; Y is selected from the group consisting of NH—CO, CO—NH, CO—NH—NH, NH—NH—CO, NH—CO—NH, CO—NH—NH—CO and S—S; the carrier protein is any suitable immunogenic protein or polypeptide. Preferably the carrier protein may comprise a T-cell epitope, and the —(CH$_2$)$_n$—X—(CH$_2$)$_y$—Y— moiety is bonded to the 3', 4' or 5' position of the nicotine molecule.

In formula (I), m is preferably 1 to 200. In another preferred embodiment, m is 1 to 20. In a particularly preferred embodiment, m is 11 to 17. In another preferred embodiment, X is selected from the group consisting of NH—CO, CO—NH, CO—NH—NH, NH—NH—CO, NH—CO—NH, and CO—NH—NH—CO.

If m is more than one, the moiety in brackets is attached m times to different points of attachment in the carrier protein. For example, if m=2, then formula (I) would be:

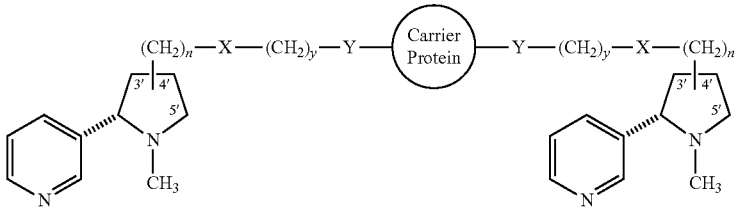

Figure 4:
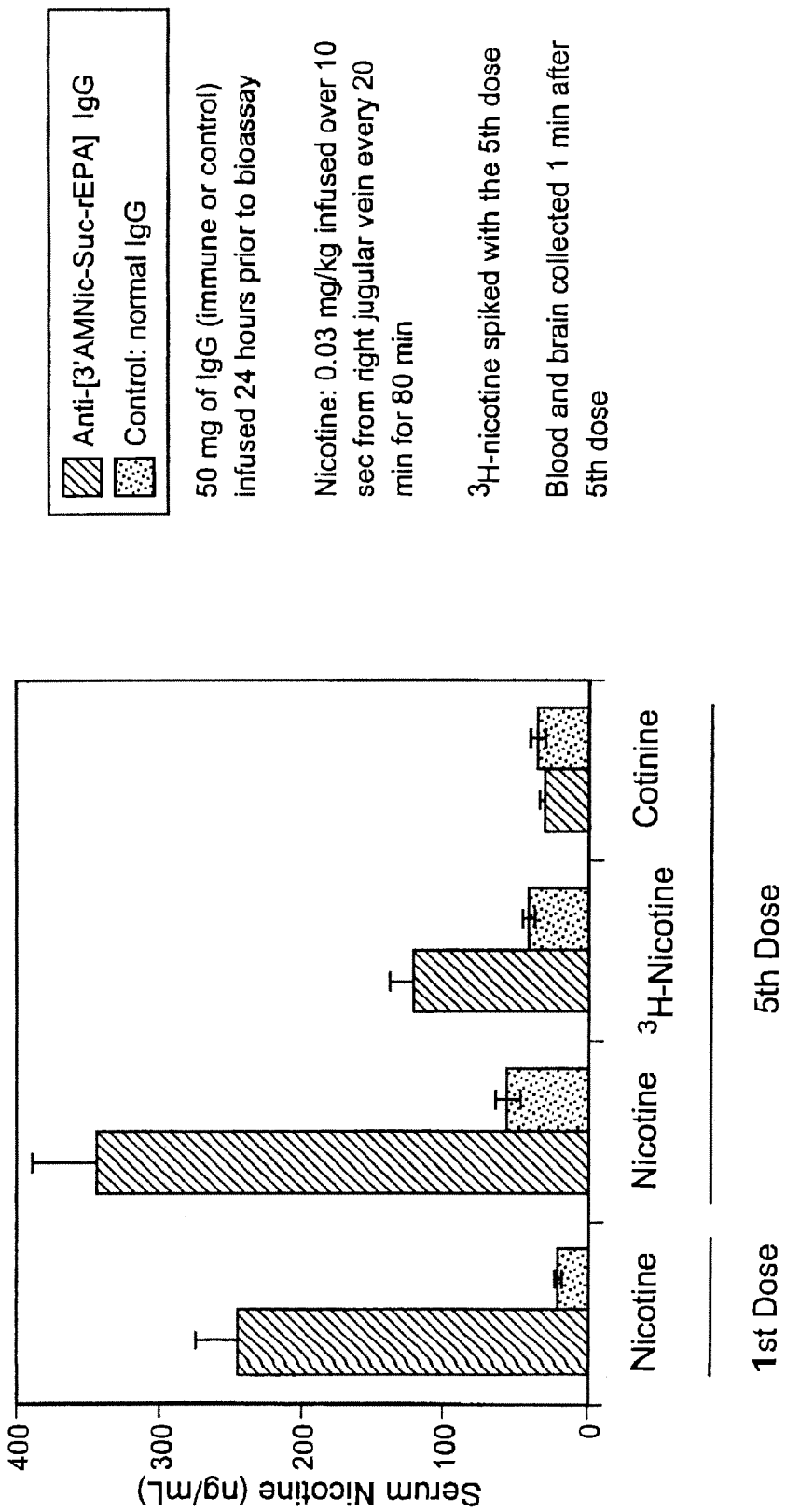

FIG. 4 shows the effect of passive immunization, with antibodies against 3'-AMNic-Suc-rEPA, on nicotine blood serum levels, in rats receiving multiple doses of nicotine.

Figure 5:
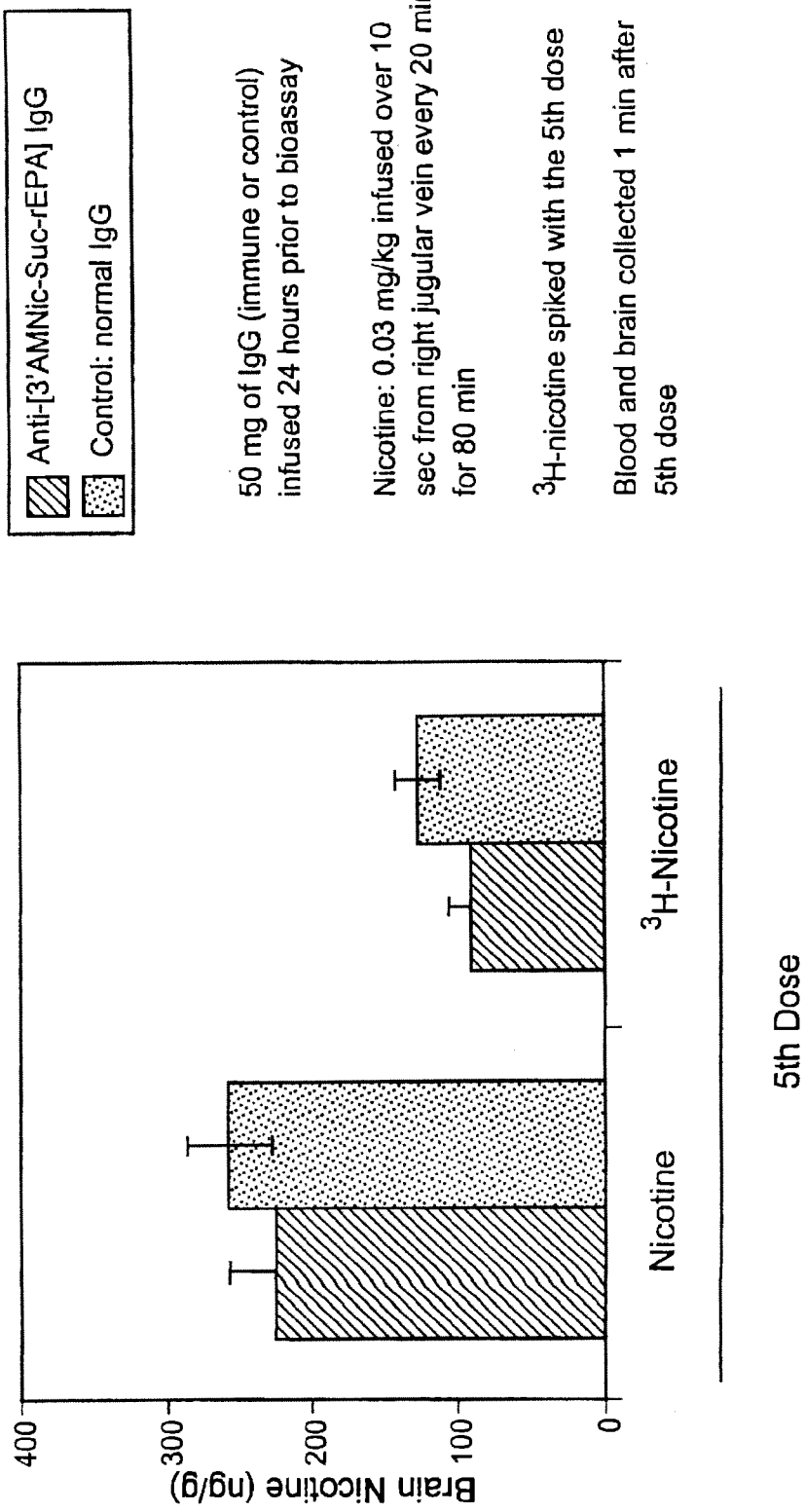

FIG. 5 shows the effects of passive immunization, with antibodies against 3'-AMNic-Suc-rEPA, on nicotine levels in rat brain, in rats receiving multiple doses of nicotine.

Figure 6:
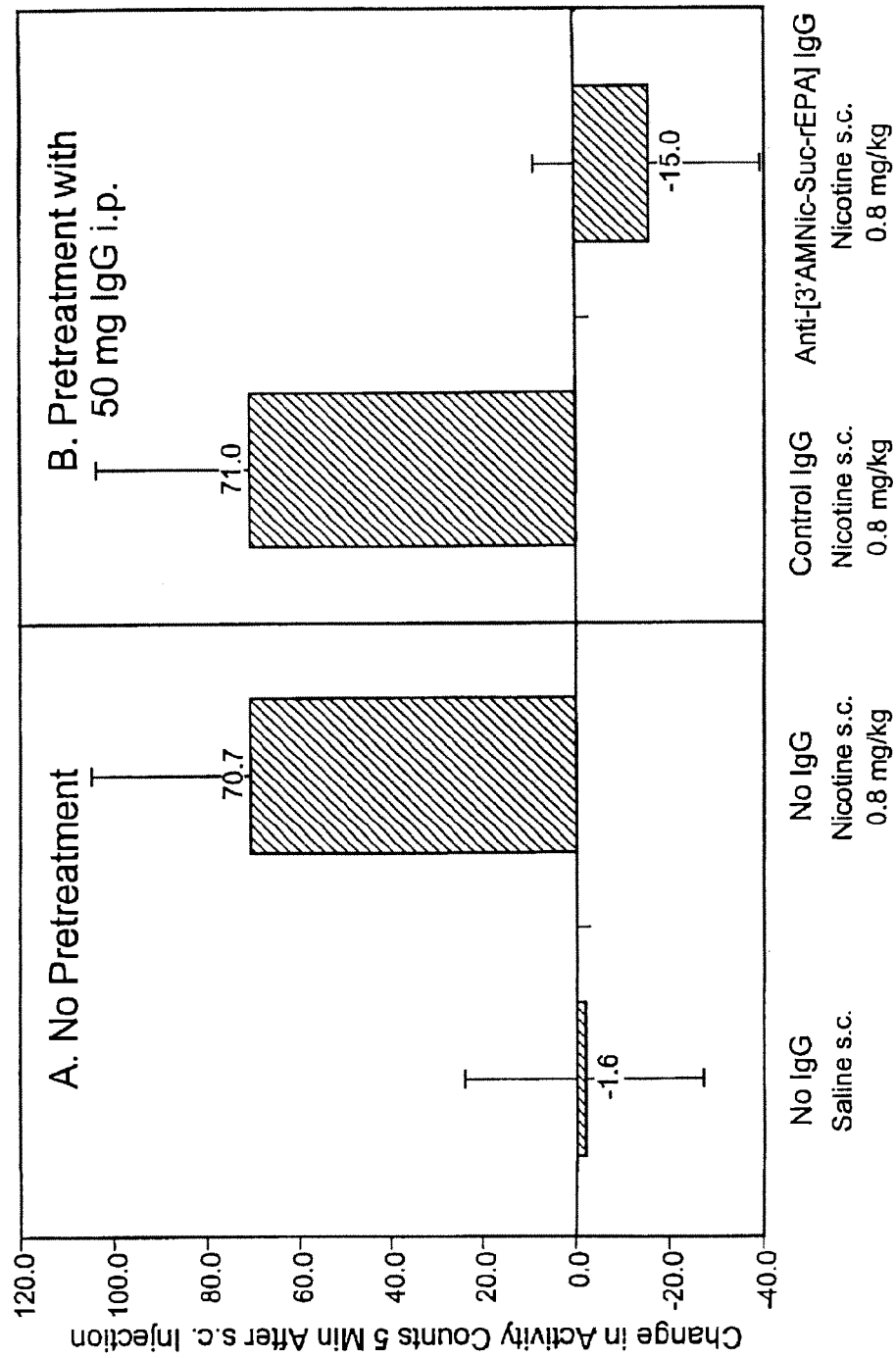

FIG. 6 shows the effects of passive immunization, with antibodies against 3% AMNic-Suc-rEPA, on nicotine-induced locomotor effects, in rats.

FIG. 7 shows the effects of passive immunization, with antibodies against 3'-AMNic-Suc-rEPA, on nicotine-induced increase in systolic blood pressure. The Figure shows that the increasing amounts of antibody increases the effectiveness of the antibodies in decreasing the nicotine-increase in blood pressure.

DETAILED DESCRIPTION OF THE PREFERRED EMBODIMENTS

The present invention provides a nicotine hapten-carrier conjugate for treating addiction to nicotine. The nicotine hapten-carrier conjugate is of formula (I):

Because antibodies cannot be raised in response to nicotine itself, the present inventors have developed a nicotine hapten which is derivatized at the 3', 4', or 5' position of nicotine. This moiety is bound to a carrier protein to yield a hapten carrier conjugate, which will raise antibodies against the nicotine moiety, when it is injected into a suitable host mammal. In this regard, in order for a pharmaceutical composition comprising the hapten carrier conjugate to induce the production of antibodies when administered to a mammal, the carrier protein must be immunogenic. Preferably, it will comprise a T cell-epitope. Thus, when the carrier protein is conjugated to the nicotine hapten, and subsequently is administered to a mammal, the mammal produces, or "raises" antibodies in response to the nicotine hapten.

Haptens and Derivatization

The term "hapten" as used in the present invention refers to a low-molecular weight organic compound that is not capable of eliciting an immune response by itself but will elicit an immune response once attached to a carrier molecule. In a preferred embodiment, the hapten is attached to the carrier via a linker. A hapten of the present invention is a nicotine derivative. This nicotine hapten contains a reactive functional group, to which the carrier can be attached directly, or via a linker, or via a matrix, or via a linker and a matrix. Preferably, the nicotine hapten is attached to the carrier protein via an amide or disulfide bond. Amide and disulfide bonds have the desirable property of stability. Because the hapten-carrier conjugates of the invention will be used as vaccines, it is important that the conjugates are stable, to prolong the shelf life of the vaccine.

In a preferred embodiment of the present invention, the nicotine hapten is represented by formula (II):

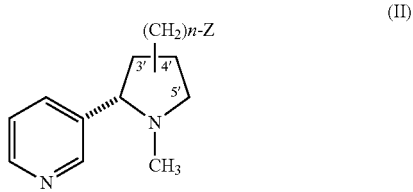

(II)

wherein n is 0 to 12 and Z is NH$_2$, COOH, CHO or SH and —(CH$_2$)$_n$—Z can be bonded to the 3', 4' or 5' position. The Z moiety is capable of binding to a carrier, directly or via a linker. The carrier-hapten conjugate will induce the production of antibodies upon its introduction into the body of a patient or an animal.

In a particularly preferred embodiment, the nicotine hapten is of the following formula (3'-ambaomethyl nicotine):

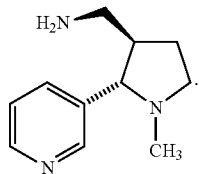

1. Direct Conjugates

To make a "direct conjugate," a single nicotine hapten is directly attached to a carrier, with or without a linker. For example, a single nicotine hapten can be attached to each available amine group on the carrier. General methods for directly conjugating haptens to carrier proteins, using a homobifunctional or a heterobifunctional cross-linker are described, for example, by G. T. Hermanson in *Bioconjugate Techniques*, Academic Press (1996) and Dick and Beurret in *Conjugate Vaccines*. Contribu. Microbiol. Immunol., Karger, Basal (1989) vol. 10, 48-114. With direct conjugation using bifunctional crosslinkers, the molar ratio of hapten to protein is limited by the number of functional groups available on the protein for the specific conjugation chemistry. For example, with a carrier protein possessing n number of lysine moieties, there will be, theoretically, n+1 primary mines (including the terminal amino) available for reaction with the linker's car) oxylic group. Thus, using this direct conjugation procedure the product will be limited to having n+1 amido bonds formed, i.e., a maximum of n+1 haptens attached.

The skilled artisan will recognize that depending on the concentration of the reactants used to conjugate the nicotine hapten to the carrier protein, and the nature of the carrier protein, the ratio of hapten to carrier will vary. Also, within a given preparation of nicotine-carrier conjugate, there will be variation in the hapten/carrier ratio of each individual conjugate. For example, exoprotein A has, in theory, 15 amines available for conjugation with hapten. However, the inventors determined that when 3' aminomethyl-succinyl-nicotine was conjugated to this protein, a range of 11-17 nicotine haptens were attached to each exoprotein A carrier, in a single preparation of conjugate. This range was experimentally determined using gas filtration chromatography and measuring the increase in UV absorbance at 260 nm. 17 nicotines were attached to some carriers because the nicotine hapten can attach to non-amine moieties on the carrier. Examples of non-amine moieties to which the hapten can attach include, but are not limited to, —SH and —OH moieties. However, the incidence of these side reactions is low.

2. Matrix Conjugates

To circumvent the limitations on the number of haptens that can be attached to carrier using direct conjugation, an amino acid "matrix" can be used. The term "matrix" denotes an amino acid, a peptide, dipeptide, or a polypeptide, including oligomeric and polymeric polypeptides. A matrix also may be a linear or branched polypeptide. Examples of amino acids that may be used to form a matrix include, but are not limited to, aspartic acid, lysine, cysteine, and L-glutamic acid. Such matrix materials may be formulated into polymers, such as poly-L-glutamic acid. When an amino acid such as cysteine is used, the thiol group is protected, thereby permitting the hapten to be linked to the carboxylic group of the amino acid. One skilled in the art would be well familiar with types of protecting groups and means of attaching protecting groups to amino acid functionalities. For a discussion, see Green, PROTECTIVE GROUPS IN ORGANIC CHEMISTRY, John Wiley & Sons, New York, 1991.

A suitable matrix possesses an appropriate functional group and is loaded with two or more haptens. Thus, in another preferred embodiment of the invention, the nicotine-substituted matrix is conjugated to the carrier protein to increase the hapten to carrier molar ratio in the hapten-carrier conjugate. The matrix plays a double role, first, as a support for a large number of haptens and, second, as a cross linker. The nicotine substituted matrix conjugated to a carrier protein is represented by formula (III):

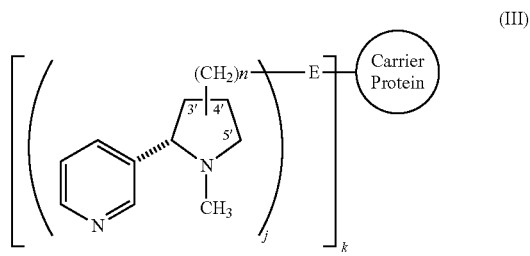

(III)

wherein n is 0 to 12, j is 1 to 1000, k is 1 to 20 E is an amino acid-containing matrix to which a hapten can be bonded, and the carrier protein is any suitable protein or polypeptide comprising a T-cell epitope. The amino acid-containing matrix E may be an amino acid, a peptide, dipeptide, or a polypeptide, including oligomeric as well as polymeric polypeptides. The matrix comprises one or more amino acids that include, but are not limited to, aspartic acid, lysine, cysteine, and poly-L-glutamic acid. In a preferred embodiment, j is 1 to 200, and in another preferred embodiment, j is 1 to 4.

Matrix-carrier conjugates are capable of forming multimeric "lattices." Such a lattice is represented in the figure below. The term "lattice" is used to denote a covalently-linked complex, comprising multiple matrices, haptens, linkers and carrier proteins, all of which are covalently linked together. Because the nicotine-substituted matrix comprises multiple nicotine moieties available for conjugation with carrier, a lattice comprising multiple carriers, and multiple nicotine-substituted matrices, can be formed. A simplified representation of a portion of such a lattice is represented as follows:

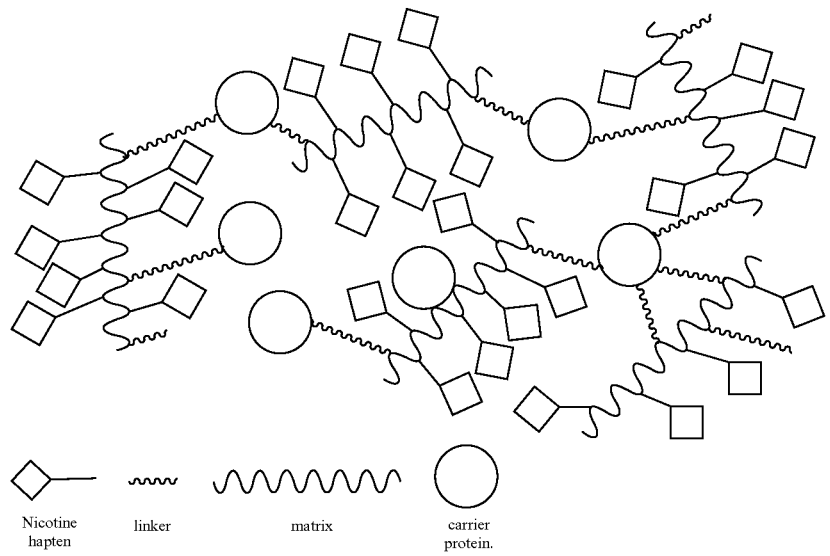

The skilled artisan will recognize that a lattice according to the invention comprises a hapten carrier conjugate of Formula (III).

This conjugation method employing a matrix offers flexibility and control over hapten to protein molar ratios regardless of the number of functional groups available for conjugation on the protein. This is particularly useful when a specific carrier protein has been used and when an optimal ratio needs to be obtained in order to achieve higher immunogenicity of the conjugate. While it is not necessary to use an when using a matrix, such a linker can be used. To use a linker with this embodiment, the nicotine substituted matrix is reacted with an active linker compound. For example, ADH, adipic acid dihydrazide, can be used as a linker with the matrix conjugates.

Carrier Proteins

Once the nicotine hapten has been prepared, it is then conjugated to a carrier protein which will be used to raise antibodies to the nicotine carrier conjugate. The carrier protein used in the present inventive nicotine carrier conjugate is represented by

in formulae (I) and (III) and encompasses any suitable immunogenic protein or polypeptide. An "immunogenic" molecule is one that is capable of eliciting an immune response. Preferably, the carrier protein will comprise a T-cell epitope. Also encompassed by the representation of a "carrier protein" are MAPs or multi-antigenic peptides, which are branched peptides. By using a MAP, hapten density and valency are maximized because of multiple branched amino acid residues. Examples of amino acids that can be used to form a MAP include, but are not limited to, lysine.

A carrier protein of the instant invention comprises a molecule containing at least one T cell epitope which is capable of stimulating the T cells of the subject, which subsequently induces B cells to produce antibodies against the entire hapten-carrier conjugate molecule. The term "epitope" as used in describing this invention, includes any determinant on an antigen that is responsible for its specific interaction with an antibody molecule. Epitopic determinants usually consist of chemically active surface groupings of molecules such as amino acids or sugar side chains and have specific three dimensional structural characteristics as well as specific charge characteristics. It is believed that to have immunogenic properties, a protein or polypeptide must be capable of stimulating T-cells. However, it is possible that a carrier protein that lacks a T-cell epitope may also be immunogenic.

By selecting a carrier protein which is known to elicit a strong immunogenic response, a diverse population of patients can be treated by the inventive hapten-carrier conjugates. The carrier protein must be sufficiently foreign to elicit a strong immune response to the vaccine. Typically, the carrier protein used preferably would be a large molecule that is capable of imparting immunogenicity to a covalently-linked hapten. A particularly preferred carrier protein is one that is inherently highly immunogenic. Thus a carrier protein that has a high degree of immunogenicity and is able to maximize antibody production to the hapten is highly desirable.

Both bovine serum albumin (BSA) and keyhole limpet hemocyanin (KLH) have commonly been used as carriers in the development of conjugate vaccines when experimenting with animals. However, these proteins may not be suitable for human use. Proteins which have been used in the preparation of therapeutic conjugate vaccines include, but are not limited to, a number of toxins of pathogenic bacteria and their toxoids. Examples include diphtheria and tetanus toxins and their medically acceptable corresponding toxoids. Other candidates are proteins antigenically similar to bacterial toxins referred to as cross-reacting materials (CRMs).

In the preparation of nicotine conjugate pharmaceutical compositions, recombinant *Pseudomonas aeruginosa* exoprotein A (rEPA) may be used as a carrier protein because its structure and biological activities have been well characterized. Moreover, this recombinant protein has been successfully and safely used in humans in the *Staphylococcus aureus* capsular polysaccharide conjugate vaccines by the National Institutes of Health and by the present inventors. Fattom et al., *Infect Immun.* 61 1023-1032 (1993). This protein has been identified as a suitable protein carrier because the intrinsic enzymatic activity of the native exotoxin has been eliminated due to an amino acid deletion at position 553. As a result, rEPA has the same immunological profile as the native exotoxin A (ETA), but does not possess the hepatotoxic properties of the native ETA. As used in this application, "exoprotein A" refers to a modified, non-hepatotoxic, ETA. On example of such an exoprotein A has an amino acid deletion at position 553.

Conjugation of Hapten to Carrier Protein

There are a large number of functional groups which can be used in order to facilitate the linking or conjugation of a carrier to a small molecule, such as a hapten. These include functional moieties such as carboxylic acids, anhydrides, mixed anhydrides, acyl halides, acyl azides, alkyl halides, N-maleimides, imino esters, isocyanates, amines, thiols, and isothiocyanates and others known to the skilled artisan. These moieties are capable of forming a covalent bond with a reactive group of a protein molecule. Depending upon the functional moiety used, the reactive group may be the e amino group of a lysine residue or a thiol group, on a carrier protein or a modified carrier protein molecule which, when reacted, results in amide, amine, thioether, amidine urea or thiourea bond formation. One skilled in the art would recognize that other suitable activating groups and conjugation techniques can be used. See, for example, Wong, *Chemistry of Protein Conjugation and Cross-Linking*, CRC Press, Inc. (1991). See also Hermanson, BIOCONJUGATE TECHNIQUES, Academic Press: 1996 and Dick and Beurret in *Conjugate Vaccines*. Contribu. Microbiol. Immunol., Karger, Basal (1989) vol. 10, 48-114.

Linear linker moieties are preferred, over cyclic or branched linkers, for conjugation of haptens to carrier proteins. A preferred linker is a succinyl moiety. However, a linker may be a cyclic structure as well as a linear moiety. Another example of a linker is ADH.

Thus, the nicotine hapten-carrier conjugates of the present invention are prepared by reacting one or more haptens with a carrier protein to yield a hapten carrier conjugate which is capable of stimulating T cells, leading to T cell proliferation and release of mediators which activate specific B cells to stimulate antibody production in response to the immunogenic hapten-carrier conjugate. Certain antibodies raised in response to the hapten carrier conjugate will be specific to the hapten portion of the hapten-carrier conjugate. The present invention contemplates the use of various suitable combinations of haptens with carrier proteins for use in the treatment of nicotine addiction.

Monoclonal and Polyclonal Antibodies

Techniques for making monoclonal antibodies are well-known in the art. Monoclonal antibodies can be obtained by injecting mice with a composition comprising the nicotine hapten-carrier conjugate, subsequently verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the hapten-carrier conjugate, culturing the clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Techniques for preparing polyclonal antibodies also are well-known in the art. Polyclonal antibodies are prepared according to standard techniques known in the art. To prepare a polyclonal antibody, an animal is injected with the immunogenic material and antibody rich serum is collected which contains therein a mixture of antibodies that are directed against numerous epitopes of the immunogen that was injected. Suitable host mammals for the production of antibodies include, but are not limited to, humans, rats, mice, rabbits, and goats.

In accordance with the present invention, functional antibody fragments also can be utilized. The fragments are produced by methods that include digestion with enzymes such as pepsin or papain and/or cleavage of disulfide bonds by chemical reduction. Alternatively, antibody fragments encompassed by the present invention can be synthesized using an automated peptide synthesizer such as those supplied commercially by Applied Biosystems, Multiple Peptide Systems and others, or they may be produced manually, using techniques well known in the art. See Geysen et al., *J. Immunol. Methods* 102: 259 (1978). Direct determination of the amino acid sequences of the variable regions of the heavy and light chains of the monoclonal antibodies according to the invention can be carried out using conventional techniques.

A fragment according to the present invention can be an Fv fragment. An Fv fragment of an antibody is made up of the variable region of the heavy chain (Vh) of an antibody and the variable region of the light chain of an antibody (Vl). Proteolytic cleavage of an antibody can produce double chain Fv fragments in which the Vh and Vl regions remain non-covalently associated and retain antigen binding capacity. Fv fragments also include recombinant single chain antibody molecules in which the light and heavy chain variable regions are connected by a peptide linker. See Skerra, a al. *Science*, 240, 1038-41 (1988). Antibody fragments according to the invention also include Fab, Fab', F(ab)$_2$, and F(ab')$_2$, which lack the Fc fragment of an intact antibody.

Therapeutic Methods

Because nicotine exerts many of its significant effects after it crosses the blood brain barrier, the present invention encompasses therapeutic methods that prevent nicotine from crossing the blood brain barrier. In particular, administration of a nicotine hapten-carrier conjugate to a patient will generate antibodies against nicotine, in the bloodstream of the patient. Alternatively, anti-nicotine antibodies generated outside the body of the patient to be treated, in a suitable host mammal, can be administered to a patient. If the patient smokes, the nicotine in his blood will be bound by the circulating anti-nicotine antibodies, preventing the nicotine from reaching the brain. Therefore, the antibodies will prevent the physiological and psychological effects of nicotine that originate in the brain. Because the smoker will experience a lessening or cessation of these effects, he/she will lose the desire to smoke. The same therapeutic effects are expected if a patient uses smokeless tobacco, after being immunized with a nicotine hapten-carrier conjugate of the invention. Additionally, the conjugates and antibodies of the invention may exert their effects by affecting the ability of nicotine to stimulate the peripheral nervous system.

As discussed above, the novel nicotine-carrier conjugates of the invention preserve the native chirality and structure of the nicotine molecule. In particular, the nicotine moiety of these conjugates has the (S)-(−) configuration. Therefore, the antibodies produced in response to such a conjugate will be specific to the native form of nicotine, and will be the most effective in specifically binding to nicotine that is inhaled from smoking or absorbed from smokeless tobacco, and in inhibiting the effects of this ingested nicotine. Additionally, the inventive conjugates are chemically stable, and stability is critical to producing a vaccine having a long shelf life.

The present vaccine composition can be used in combination with compounds or other therapies that are useful in the treatment of addiction. This includes administration of compounds which include, but are not limited to, anti-depressant drugs such as ZYBAN® (bupropion) and PROZAC® (fluoxetine).

1. Administration of a Nicotine Hapten-Carrier Conjugate

The conjugates of the invention are suitable for treating and preventing nicotine addiction. For treating nicotine addiction, a nicotine-carrier conjugate of the invention is administered to a patient suffering from nicotine addiction. For preventing nicotine addiction, patients at risk for developing nicotine addiction, such as teenagers, are treated with a conjugate according to the invention. Direct administration of the conjugate to a patient is called "active immunization."

A vaccine composition of the present invention comprises at least one nicotine hapten-carrier conjugate in an amount sufficient to elicit an immune response thereto. The nicotine hapten carrier conjugate is capable of remaining in vivo at a concentration sufficient to be active against subsequent intake of nicotine.

Initial vaccination with the nicotine hapten carrier conjugate of the present invention creates high titers of antibodies that are specific to nicotine. The therapeutically effective amount of a conjugate which is administered to a patient in need of treatment for nicotine addiction is readily determined by the skilled artisan. Suitable dosage ranges are 1-1000 µg/dose. It generally takes a patient one to several weeks to generate antibodies against a foreign antigen. The production of antibodies in a patient's blood can be monitored by using techniques that are well-known to the skilled artisan, such as ELISA, radioimmunoassay, and Western blotting methods. Therapeutic effectiveness also can be monitored by assessing various physical effects of nicotine, such as blood pressure.

As described in detail below, the inventive nicotine hapten-carrier conjugates can be processed to afford a composition which can be readily administered to a patient. The preferred modes of administration include but are not limited to intranasal, intratracheal, oral, dermal, transmucosal subcutaneous injection and intravenous injection. The skilled artisan will recognize that the initial injection may be followed by subsequent administration of one or more "boosters" of conjugate. Such a booster will increase the production of antibodies against the nicotine hapten-carrier conjugate of the invention.

The vaccine compositions of the present invention may contain at least one adjuvant. The adjuvant used in the present invention will be selected so that the effect of the carrier protein is not inhibited. Adjuvants used in the present invention are those which are physiologically acceptable to humans, these include, but are not limited to, alum, QS-21, saponin and MPLA (monophosphoryl lipid A).

The vaccine compositions of the present invention may optionally contain one or more pharmaceutically acceptable excipients. The excipients useful in the present include sterile water, salt solutions such as saline, sodium phosphate, sodium chloride, alcohol, gum arabic, vegetable oils, benzyl alcohols, polyethylene glycol, gelatin, mannitol, carbohydrates, magnesium stearate, viscous paraffin, fatty acid esters, hydroxy methyl cellulose and buffers. Of course, any additional excipients known to the skilled artisan are useful in the present invention.

The hapten-carrier conjugates of the present invention, in order to be administered to a patient in need of treatment or prevention of nicotine addiction, are incorporated into a pharmaceutical composition. When the composition containing the hapten-carrier conjugate is to be used for injection, it is preferable to solubilize the hapten-carrier conjugate in an aqueous, saline solution at a pharmaceutically acceptable pH. However, it is possible to use an injectable suspension of the hapten-carrier conjugate. In addition to the usual pharmaceutically acceptable excipients, the composition may contain optional components to ensure purity, enhance bioavailability and/or increase penetration.

Additionally, the vaccine composition may optionally contain at least one auxiliary agent, such as dispersion media, coatings, microspheres, liposomes, microcapsules, lipids, surfactants, lubricants, preservatives and stabilizers. Of course, the any additional auxiliary agents known to the skilled artisan are useful in the present invention. Also useful herein are any agents which act to synergize the effect of the present vaccine composition.

The pharmaceutical composition of the present invention is sterile and is sufficiently stable to withstand storage, distribution, and use. Additionally, the composition may contain additional components in order to protect the composition from infestation with, and growth of, microorganisms. It is preferred that the composition is manufactured in the form of a lyophilized powder which is to be reconstituted by a pharmaceutically acceptable diluent just prior to administration. Methods of preparing sterile injectable solutions are well known to the skilled artisan and include, but are not limited to, vacuum drying, freeze-drying, and spin drying. These techniques yield a powder of the active ingredient along with any additional excipient incorporated into the pre-mix.

2. Administration of Antibodies Produced in Response to a Nicotine-Carrier Conjugate Passive immunization comprises administration of or exposure to a polyclonal antibody or monoclonal antibody which has been raised in response to a nicotine hapten carrier conjugate of the invention. Such antibodies can be generated in animals or humans. Antibodies raised in response to a nicotine conjugate of the invention can be administered to prevent addiction to nicotine. For example, such antibodies can be administered to people considered to be at risk for developing addiction to nicotine, such as teenagers. Antibodies also are suitable for treating a patient addicted to nicotine. As discussed above, the antibodies will bind nicotine in the blood, and prevent nicotine from crossing the blood brain barrier. Antibodies raised by administration of the inventive hapten-carrier conjugate have a molecular weight range of from about 150 kDa to about 1,000 kDa.

The therapeutically effective amount of a therapeutic antibody of the invention which is administered to a patient in need of treatment for nicotine addiction is readily determined by the skilled artisan. Suitable dosage ranges are 1-1000 µg/dose.

A therapeutic composition of the present invention comprises at least antibody produced in response to a nicotine-carrier conjugate of the invention. These compositions of the present invention may optionally contain one or more pharmaceutically acceptable excipients. The excipients useful in the present include sterile water, salt solutions such as saline, sodium phosphate, sodium chloride, alcohol, gum arabic, vegetable oils, benzyl alcohols, polyethylene glycol, gelatin, mannitol, carbohydrates, magnesium stearate, viscous paraffin, fatty acid esters, hydroxy methyl cellulose and buffers. Of course, any additional excipients known to the skilled artisan are useful in the present invention.

The antibodies of the present invention, in order to be administered to a patient in need of treatment or prevention of nicotine addiction, are incorporated into a pharmaceutical composition. When the composition containing an antibody is to be used for injection, it is preferable to have the antibody in an aqueous, saline solution at a pharmaceutically acceptable pH. However, it is possible to use an injectable suspension of the antibody. In addition to the usual pharmaceutically acceptable excipients, the composition may contain optional components to ensure purity, enhance bioavailability and/or increase penetration.

A pharmaceutical composition comprising an antibody of the present invention is sterile and is sufficiently stable to withstand storage, distribution, and use. Additionally, the composition may contain additional components in order to protect the composition from infestation with, and growth of, microorganisms. Methods of preparing sterile injectable solutions are well known to the skilled artisan and include, but are not limited to, vacuum drying, freeze-drying, and spin drying. These techniques yield a powder of the active ingredient along with any additional excipient incorporated into the pre-mix.

Kits Comprising Antibodies of the Invention

The antibodies of the present invention also are useful in preparing a kit that can be used to detect and quantify nicotine levels in a sample. A kit according to the invention comprises a nicotine-specific antibody according to the invention, in a suitable container. For a radioimmunoassay, the kit may also comprise labeled nicotine. Nicotine in a sample is detected by binding labeled nicotine to the antibody, and then competing the labeled nicotine from the antibody with the sample to be tested. An ELISA kit also would comprise an antibody according to the invention. The ELISA may involve inhibition of antibody binding with known amounts of nicotine compared to inhibition with a sample suspected of containing nicotine. This would allow determination of unknown nicotine in a sample, by comparison of sample with the standard inhibition curve of known nicotine concentration. In another type of ELISA, a sample suspected of containing nicotine would be incubated with a microliter plate that has been coated with a substance that will bind nicotine. The antibodies of the invention would be added, and enzyme-linked anti-antibody antibodies would be added to the plates. Addition of substrate would quantify the amount of nicotine bound to the plate.

The following examples are provided merely to further illustrate the preparation and use of the present invention. The scope of the invention is not limited to the following examples.

Example 1

Synthesis of a Derivitized Nicotine Hapten
(Substituted at the 3' Position)

The starting material for the synthesis of the hapten is trans-4'-carboxy-(−)-cotinine, available from commercial sources. A modification of the procedure described by Cushman and Castagnoli, Jr. (1972) *J. Org. Chem.* 37(8):1268-1271 provides the alcohol, trans-3'-hyciroxymethyl-(−)-nicotine, after methyl esterification of the acid followed by reduction of the ester. The alcohol is then sulfonated and the sulfonate is displaced with an azido group, which is finally reduced to an amine.

4 g of trans-4'-carboxy-(−)-cotinine are dissolved in 50 mL of a solution of 2 N sulfuric acid in dry methanol and stirred overnight at room temperature. The resulting suspension is filtered through a Whatman No. 1 filter paper and added slowly to 100 mL of a saturated solution of sodium bicarbonate. The ester is extracted with dichloromethane to afford 4.2 g of a pink oil after solvent evaporation.

A solution of 3.9 g of the ester in dry tetrahydrofuran (100 mL) is added dropwise to a suspension of 4 equivalents of lithium aluminum hydride in dry tetrahydrofuran (70 mL) under dry argon. The suspension is stirred for two hours at room temperature. Excess hydride is destroyed by careful and controlled addition of water while cooling in an ice bath. The resulting white precipitate is filtered off and the filtrate dried over sodium sulfate and concentrated under reduced pressure to afford 2.7 g of the alcohol as a yellow oil.

The alcohol (1.9 g) is dissolved in 20 mL of dichloromethane. Triethylamine (0.75 mL) and p-toluenesulfonyl chloride (1 g) are then successively added to the solution. The orange solution is stirred for 24 hours at room temperature. Precipitated triethylamine hydrochloride is filtered off on a Celite bed and the filtrate is concentrated under reduced pressure to give a brown oil. The sulfonate is purified on a silica flash chromatography column eluted with 5% methanol in dichloromethane to give 2.1 g of a yellow oil.

The sulfonate (1.8 g) is displaced using sodium azide (0.8 g) in 50 mL dimethylformamide for one hour at 80° C. After evaporation of dimethylformamide under high vacuum, the residue is dissolved in dichloromethane, washed with water and brine and dried over sodium sulfate. After solvent evaporation, the azide (1.1 g) is obtained as a brownish oil.

The addition of the azide in dry tetrahydrofuran (20 mL) to a suspension of lithium aluminum hydride in dry tetrahydrofuran (50 mL) readily produced the desired amine as monitored by thin layer chromatography. Proton and carbon nuclear magnetic resonance spectra of the purified amine corresponded to the expected structure.

Example 2

Synthesis of a Derivitized Nicotine Hapten
(Substituted at the 4' Position)

Introduction of a functionalized arm on position 4' of nicotine can be achieved by enolate alkylation of cotinine followed by reduction of the alkylated product. Various alkylating agents can be used like an appropriately protected 3-bromo-propylamine. As examples, 3-bromo-N-carbobenzyloxy-propylamine or N-(3-bromopropyl)-phtalamide can be used. The amine protecting group will have to be removed after alkylation and reduction and prior to conjugation to a carrier protein. Enolate alkylation of cyclic lactams (containing the pyrrolidinone ring) is well documented in the literature (see G. Helmchen et al. (1995) Steroselective Synthesis in *Houben-Weyl-Methods of Organic Chemistry*, Vol. E21a, 762-881, Thieme, Stuttgart, Germany, for a general review, and A. J. Meyers a al. (1997) *J. Am. Chem. Soc.,* 119, 4564-4566, for steric considerations of the reaction). There are also some examples of enolate alkylation of cotinine itself (N.-H. Lin et al. (1994) *J. Med. Chem.,* 37, 3542-3553). An interesting preparation of 4'-acetyl-nicotine, as a 1:1 mixture of two epimers, was achieved using a tandem cationic aza-Cope rearrangement-Mannich cyclization reaction starting from a ketone (or an aldehyde) and a 2-alkoxy-3-alkenamine (L. E. Overman (1983) *J. Am. Chem. Soc.*, 105, 6622-6629). This reaction can be extended to produce 4'-aldehydo-nicotine, suitable for conjugation.

3-bromo-propylamine hydrobromide (4.2 g) was suspended in 50 mL dichoromethane and triethylamine (about 7 mL) was added until a clear solution was obtained. The solution was cooled to 0° C. and benzyl chloroformate (2.5 mL) was added dropwise. The reaction was allowed to proceed at room temperature for 16 hours under stirring. The precipitating salts were filtered off and the clear organic layer was washed with cold water, cold 1 N HCl and cold water, dried on sodium sulfate and evaporated under reduced pressure to a yellow oil (2.93 g of crude material).

Cotinine (62 mg) and 3-bromo-N-carbobenzyloxy-propylamine (100 mg) were separately co-evaporated with dry toluene. Cotinine was dissolved in 5 mL of freshly distilled anhydrous tetrahydrofuran, 60 µL of N,N,N',N'-tetramethylenediamine (TMEDA) were added and the solution cooled to −78° C. by immersion in an ethanol-dry ice bath. The cotinine solution was added dropwise to a solution of lithium diisopropylamide (LDA, 200 µL of a 2 M solution in heptane-tetrahydrofuran) in tetrahydrofuran, previously cooled to −78° C. The orange mixture is stirred for 15 minutes at −78° C. and then left to warm up in an ice bath (2 to 6° C.). The reaction was then cooled again to −78° C. and 3-bromo-N-carbobenzyloxy-propylamine dissolve in anhydrous tetrahydrofuran added dropwise for 15 minutes. The reaction mixture was left to warm-up to −10° C. and then quenched with methanol. The reaction product was purified by flash chromatography on a silica gel column. Reduction of the amide of this cotinine derivative was achieved with borane followed by cesium fluoride in hot ethanol. The final amine was obtained after removal of the carbobenzyloxy group in acidic conditions.

Example 3

Synthesis of a Derivitized Nicotine Hapten
(Substituted at the 5' Position)

Introduction of a functionalized arm on position 5' of nicotine can be achieved by reacting appropriately protected alkyl lithium compounds with cotinine, followed by reduction with sodium cyanoborohydride, in procedures similar to those described by Shibagaki et al. (1986) *Heterocycles*, 24, 423-428 and N.-H. Lin et al. (1994) supra.

Example 4

Conjugation of a Derivitized Nicotine Hapten to a Carrier Protein

Recombinant exoprotein A (rEPA) is linked to the derivitized nicotine hapten through a succinic acid arm. The 15 lysines of rEPA were readily succinylated with succinic anhydride. Then, in a typical conjugation reaction, a 5 to 10 mg/mL solution of the succinylated recombinant exoprotein A (Suc-rEPA) in a 2-(N-morpholino) ethanesulfonic acid (MES) buffer 0.05 M containing 0.15 M NaCl at pH 6.0 was prepared. An equal weight of 3'-aminomethyl-(−)-nicotine (3'AMNic) hapten dissolved in a minimal amount of distilled water was added to the protein solution. The pH of the hapten solution was adjusted to 6.0 with 0.1 N HCl before addition. Finally, an equal weight of 1-ethyl-3-(3-diethylamino)propyl carbodiimide hydrochloride (EDC) was added to the hapten protein mixture and the reaction proceeded for 30 min at room temperature while stirring. The thus obtained nicotine conjugate was purified on a Sephadex G-25 column eluted with phosphate buffer saline (PBS) at pH 7.4. Conjugate recoveries were in the 80 to 90% range.

Example 5

Conjugation of Nicotine-Loaded Matrix

This example describes synthesis of a hapten-carrier conjugate comprising 3'-aminomethyl-(−)-nicotine as a deriv-itized hapten, recombinant exoprotein A (rEPA) as a carrier protein, adipic acid dihydrazide (ADH) as a linker and poly-L-glutamic acid as a "matrix," or polymer support, for the haptens A poly-L-glutamic acid having an average molecular weight of 39,900 with a polydispersity of 1.15 and a degree of polymerization of 264 was used in this example. The reacting amounts of hapten and polymer were calculated so that the target degree of substitution is about 80%. That is, when 80% substitution is reached, about 208 hapten units were conjugated, out of a total 264 repeat units in an average molecule of the glutamic acid polymer.

This nicotine-loaded poly-L-glutamic acid has the following formula:

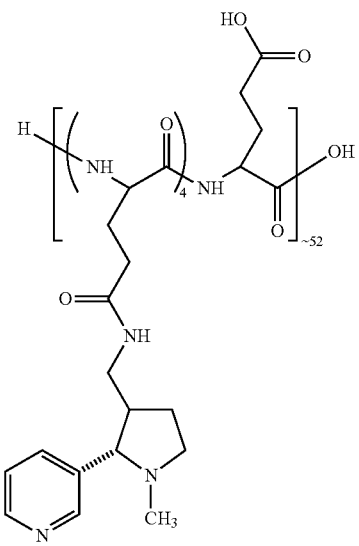

As indicated in the figure, the polyglutamic acid polymer comprises about 52 glutamine residues. This number will vary, depending on the batch and source of the polyamino acid residue chosen for the matrix. Also, the figure indicates that 4 nicotine haptens for each repeating unit. This number will vary depending on the ratio of reactants used when the matrix and the nicotine hapten are conjugated.

Following conjugation with the derivitized nicotine, the unreacted carboxylic groups (about 20%) were then derivatized with ADH. When this matrix was conjugated to a carrier, as described in Example 6, the molar ratio of the nicotine-loaded matrix to protein was 1:1. Thus, in this conjugate, the theoretical nicotine hapten to protein molar ratio would be 200:1, at the completion of the conjugation reaction.

The actual ratio of nicotine substitution on the polyglutamic acid was estimated using NMR analysis of the product. The intensity of the glutamic acid α-hydrogen peak relative to the four hydrogens of the pyridine ring of the nicotine provide the proportion of nicotine incorporated. The estimated average ratio was 143:1 (nicotine/carrier protein).

Example 6

Preparation of a Nicotine Conjugate Vaccine Using Nicotine-Loaded Matrix

A. Loading the Nicotine Hapten on the Matrix 10 mg of poly-L-glutamic acid salt (Sigma, Cat #P-4761) were dissolved in 2 mL of 0.05 M 2-(N-morpholino)ethansulfonic acid (MES) buffer containing 0.15 M NaCl at pH 6.0. 10 mg of 3'-aminomethyl-(−)-nicotine were dissolved in a minimal amount of distilled water and the pH of the solution was adjusted to pH 6.0 with 0.1N HCl. The nicotine hapten solution was added dropwise to the polypeptide solution while stirring and was subsequently adjust to a pH of 6.0. 20 mg of solid 1-ethyl-3-(3-dimethylaminopropyl) carbodiimide hydrochloride (EDC) were then added in three portions to the hapten-polypeptide mixture over a period of 20 minutes. The reaction was allowed to proceed for one hour at room temperature. The reaction product (nicotine-substituted matrix) was dialyzed against three changes of water and lyophilized. 12 mg of nicotine-substituted polyglutamic acid were obtained as a white fluffy material.

B. Attachment of the Linker to the Nicotine-Substituted Matrix 10 mg of nicotine-substituted polyglutamic acid were dissolved in 2 mL of MES buffer at pH 6.0. 8 mg of adipic acid dihydrazide (ADH) followed by 10 mg of EDC were added to the solution while stirring. The reaction was allowed to proceed for 1 hour at room temperature. The obtained solution was finally dialyzed against three changes of MES buffer at pH 6.0.

C. Conjugation to the Carrier Protein 10 mg of recombinant exoprotein A (rEPA) were dissolved in 2 mL of 0.05 M MES buffer at pH 5.6 containing 0.15 NaCl. A volume of ADH-bound micotine-substituted polyglutamic acid solution estimated to contain 7.5 mg of this derivatized material was added to the protein solution. Solid EDC was added to this mixture in three portions over a period of 20 minutes while stirring at room temperature. The reaction was allowed to proceed at room temperature overnight. The resulting conjugate was finally purified on a Sephadex G-25 column, and eluted with phosphate buffered saline (PBS) at pH 7.4. This produces a purified preparation of conjugate, wherein the conjugate contains only the (S)-(−) form of nicotine.

Example 7

Characterization of the Nicotine Carrier Conjugate of Example 4

The purified conjugate vaccine of Example 4 was analyzed on a Superose 12 size exclusion chromatography column and eluted with PBS at pH 7.4. The hapten to protein molar ratio of 11 to 17 was calculated by determining the increase of the UV absorption at 260 nm after the incorporation of nicotine, relative to the absorption at 280 nm. This range was determined by calculating the hapten/carrier protein ratio of six separate prepared lots of hapten-carrier conjugate (lot 1: 17.2, lot 2: 16.2, lot 3: 13.2; lot 4: 12.0; lot 5: 11.0; lot 6: 17.2).

Further analysis to determine this ratio using MALDI-TOF mass spectrometry gave essentially the same numbers as obtained by UV absorbance difference. The protein concentration of the conjugate vaccine was determined using a BCA assay. A stability study of the nicotine-carrier conjugate of example 4 was carried out. The study used the vaccine vialed in 1 mL glass vials at a concentration of 0.5 mg/mL and the stability of the vialed vaccine was tested at three different temperatures: −70° C., 2 to 8° C. and room temperature.

Example 8

Stability of the Nicotine Carrier Conjugate of Example 4

The conjugation procedure based on the formation of amide bonds between hapten-linker-carrier rather than ester bonds appeared beneficial as observed in the stability of the conjugate for six months at −70° C., 2 to 8° C. and even at room temperature. The stability study consisted of monitoring and assaying the conjugate vaccine using the following:

1.) Visual observation to look for any particulates formed (turbidity, precipitation).
2.) Checking for any significant pH change.
3.) Size exclusion chromatography profile in combination with UV absorption at 260 and 280 nm to determine if the ratio of nicotine incorporation changed.
4.) Reversed phase chromatography to check for any carrier protein degradation.
5.) SDS PAGE with silver staining looking for any proteolytic cleavage of the conjugated protein.

The conjugation procedure based on the formation of an amide bond between the hapten and the linker as well as between the linker and the carrier appeared beneficial as observed in the stability of the conjugate for six months at −70° C. and 2 to 8° C.

Example 9

Evidence of Immunogenicity of the Carrier Conjugate of Examples 4 and 6

Two nicotine hapten-carrier conjugate vaccines were used to immunize mice, rats, and rabbits.

A. Animal Tests-Polyclonal Antibodies

Animals were immunized using standard protocols. In mice, three subcutaneous injections of vaccine were administered, two weeks apart, with test bleeds performed one week following the first and second injection, and exsanguination occurring one week following the third injection. Serum samples were evaluated in an ELISA assay, described in Example 10. The ELISA assay utilized 3' AMNic-pGlu bound to microliter plates.

Rats were immunized intraperitoneally with the vaccines three times. Injections were given two weeks apart with test bleeds performed one week following the first and second injection. The rats were then exsanguinated one week after the third injection. Freund's complete adjuvant was used for the first injection, and incomplete Freund's adjuvant for the subsequent injections. Serum samples were evaluated in an ELISA assay.

Rabbits were immunized intramuscularly three times, three weeks apart with 100 μg of vaccine. The initial injection contained Freund's adjuvant, with subsequent injections containing incomplete Freund's adjuvant. Rabbits were test bled one week following the second and third injections to ensure adequate titers for production bleeding. If adequate titer was acquired as measured by ELISA, rabbits were then placed on a weekly production bleed schedule (20 to 40 mL serum per rabbit). Antibody titers were monitored over time and animals were boosted if necessary to restore antibody levels.

The results of these immunogenicity studies are shown in Tables 1-5. Tables 1 and 2 show the results of an immunogenicity study in mice. In Table 1, the conjugate used was 3' aminomethyl-(−)-nicotine-succinyl-rEPA (Example 4). In Table 2, the conjugate used was 3-aminomethyl-(−)-nicotine-polyglutamic acid-ADH-rEPA (Example 6). These Tables show generation of high titers of antibodies that specifically bind nicotine. Furthermore, these conjugates showed the ability to induce the booster response.

Tables 3 and 4 show the results of an immunogenicity study in rats. In Table 3, the conjugate used was 3' aminomethyl-(−)-nicotine-succinyl-rEPA (Example 4). In Table 4, the conjugate used was 3-aminomethyl-(−)-nicotine-polyglutamic acid-ADH-rEPA (Example 6). These Tables show generation of high titers of antibodies that specifically bind nicotine. Furthermore, these conjugates showed the ability to induce the booster response.

Table 5 shows the results of an immunogenicity study in rabbits. Using either 3' aminomethyl-succinyl-rEPA (Example 4) or 3-aminomethyl-polyglutamic acid-ADH-rEPA (Example 6), high titers of antibodies were generated against the two conjugate. Those titers remained elevated for more than 6 months.

TABLE 1

Treatment of mice with 3'AMNic-Suc-rEPA

| Number of Animals | Dose | Titer | | |
|---|---|---|---|---|
| | | 1 injection | 2 injections | 3 injections |
| 10 | 1 µg | 0 | 36 | 4,280 |
| 10 | 5 µg | 1 | 884 | 10,727 |
| 10 | 15 µg | 3 | 2,476 | 14,160 |

Dose is based on protein assay
Titer is the arithmetic mean, one week after corresponding injection.

TABLE 2

Treatment of mice with 3'AMNic-pGlu-ADH-rEPA

| Number of Animals | Dose | Titer | | |
|---|---|---|---|---|
| | | 1 injection | 2 injections | 3 injections |
| 10 | 2 µg | 2 | 739 | 6,586 |
| 10 | 10 µg | 2 | 2,490 | 9,573 |
| 10 | 30 µg | 11 | 2,822 | 8,195 |

Dose is based on dry weight of lyophilized conjugate
Titer is the arithmetic mean, one week after corresponding injection.

TABLE 3

Treatment of rats with 3'AMNic-Suc-rEPA

| Number of Animals | Dose | Titer | | |
|---|---|---|---|---|
| | | 1 injection | 2 injections | 3 injections |
| 3 | 15 µg | 18 | 7,942 | 9,947 |
| 3 | 25 µg | 4 | 1,446 | 5,991 |
| 3 | 50 µg | 353 | 7,211 | 8,996 |

Dose is based on protein assay
Titer is the arithmetic mean, one week after corresponding injection.

TABLE 4

Treatment of rats with 3'AMNic-pGlu-ADH-rEPA

| Number of Animals | Dose | Titer | | |
|---|---|---|---|---|
| | | 1 injection | 2 injections | 3 injections |
| 5 | 100 µg | 0 | 1,067 | 3,752 |

Dose based on dry weight of lyophilized conjugate Arithmetic mean, one week after corresponding injection

TABLE 5

Treatment of rabbits with 3'AMNic-Suc-rEPA and 3'AMNic-pGlu-ADH-rEPA

| Immunogen | Number of Animals | Dose | Titer |
|---|---|---|---|
| 3'-AMNic-Suc-rEPA | 10 | 100 µg | 132,000 |
| 3'AMNic-pGLu-ADH-rEPA | 10 | 100 µg | 147,000 |

Dose based on protein assay for 3'AMNic-Suc-rEPA and on dry weight for 3'-AMNic-pGlu-rEPA
Titer is arithmetic mean, six to seven weeks after third injection Example 10

ELISA Assay and Antibody Specificity

The nicotine molecule itself is not suitable for coating ELISA plates and needs to be linked to a larger molecule having better adhesive properties. Poly-L-lysine or poly-L-glutamic acid are commonly used for this purpose. The derivitized nicotine hapten 3'-aminomethyl-(−)-nicotine (3'AMNic) was conjugated to poly-L-glutamic acid and the 3'-aminomethyl-(−)-nicotine-poly-L-glutamic acid conjugate (3'AMNic-pGlu) obtained was used to coat the ELISA plates.

Antibodies generated against 3'AMNic vaccine were evaluated using a 3'AMNic-pGlu ELISA as follows: Dynatech Immulon 4 microtiter plates (Chantilly, Va.) were coated 100 µL/well with 10 ng/mL 3'AMNic-pGlu in 0.1 M bicarbonate buffer, pH 9.6 and allowed to incubate overnight (ON) at room temperature (RT). The plates were then aspirated and blocked with 1% BSA in PBS for one hour at RT. Samples and reference serum were diluted in PBB (1% BSA, 0.3% BRIJ in PBS, pH 7.2) to a dilution which results in an approximate optical density (OD) at 450 nm of 2.0. The plates were washed (9% NaCl, 0.1% BRIJ) five times and diluted samples and reference serum were loaded. The reference and samples were 2-fold diluted down the plates for a final volume of 100 µL/well and plates are incubated for 1 hour at 37° C. The plates were then washed again and loaded 100 µL/well with peroxidase-conjugated anti-species IgG, Fc specific (Jackson, West Grove, Pa.) diluted in PBB and incubated at 37° C. for one hour. The plates were washed and incubated 10 minutes at RT with 100 µl/well 3,3', 5,5'-tetramethylbenzidine (TMB) substrate (KPL, Gaithersburg, Md.) diluted 1:1 with $H_2O_2$ (supplied with TMB reagent kit). The reaction is stopped with the addition of 100 µL/well 1 M phosphoric acid and read at 450 nm on an MR4000 microtiter plate reader (Dynatech). Samples are quantified in relation to the reference using parallel line analysis. The reference is assigned a numerical value (U/mL) that corresponds to the dilution which gives an OD of approximately 2.0 at 450 nm.

Antibody specificities were evaluated using an inhibition ELISA assay. Each anti-[3' AMNic-Suc-rEPA] serum was diluted to a concentration twice that which would results in an optical density of about 2.0 at 450 nm. Using the 3' AMNic-pGlu ELISA described above, the diluted antiserum to be tested was absorbed 1:1 (v/v) with increasing amounts of test antigen (inhibitor) for three hours at 37° C., and that absorbed sample was tested in the ELISA using unabsorbed serum as a reference. Percent absorption with reference to the unabsorbed sample was determined for each sample.

The specificity of rat serum containing antibodies raised in response to 3' AMNic-Suc-rEPA, using inhibition ELISA with nicotine tartrate as inhibitor, was calculated. The $IC_{50}$ for this antibody was $3.5\times10^{-6}$ M. The specificity of rabbit serum containing antibodies raised in response to 3' AMNic-Suc-rEPA, using inhibition ELISA with nicotine tartrate as inhibitor, was calculated. The $IC_{50}$ for this antibody was $2.3\times10^{-5}$ M.

Example 11

Antibody Affinity and Binding Capacity

Antibody binding capacity was measured using equilibrium dialysis for 4 hours at 37° C. using 0.7 mL of plasma, Teflon semi-micro cells, Spectrapor 2 membranes with a molecular weight cutoff of 12 to 14 kD and Sorenson's buffer (0.13 phosphate, pH 7.4) see Pentel et al., *J. Pharmacol. Exp. Ther.* 246, 1061-1066 (1987). Plasma pH was measured at the end of reach equilibrium dialysis run, and samples were used only if the final pH is 7.30 to 7.45.

Antibody affinity for nicotine was calculated using a soluble radioimmunoassay, see Mueller, *Meth. Enzymol.*, 92, 589-601 (1983). The molecular weight of IgG was measured to be 150 kD.

The binding constants and affinities obtained with the radioimmunoassay were as follows. For anti-[3' AMNic-Suc-rEPA] rat serum, the $IC_{50}$ (Molar) was $1.36\times10^{-7}$. The K (Molar-1) was $2.57\times10^{7}$. Binding sites concentration was $2.61\times10^{-6}$ binding sites/L and nicotine-specific IgG concentration was 0.2 mg/mL.

Example 12

Evaluation of Nicotine Distribution in Plasma and Brain of Animal Models

The present inventive vaccine has been evaluated in various animal models. Rat models were used to determine the effect of active or passive immunization on nicotine distribution in plasma and brain. One study examined the effects of passive immunization on attenuation of the locomotor effects of nicotine, which are a central nervous system (CNS) action of nicotine. Another experiment evaluated the effects of passive immunization on the effects of nicotine on the cardiovascular system: elevation of the systolic blood pressure.

To evaluate the present immunotherapy, an animal model has been developed to simulate the rapid absorption of nicotine from two cigarettes in humans. This animal model is described in Hieda (1997) *J. Pharmacol. Exp. Ther.* 283(3): 1076-1081. In this model, rats were administered 0.03 mg/kg of nicotine by i.v. infusion over 10 sec., simulating the rapid absorption of nicotine from the lungs in human smokers. Blood samples were taken at 3 and 10 min after nicotine injection for measurement of plasma nicotine. When brain nicotine concentrations were to be determined, animals were sacrificed 3 rain after nicotine injection, and their brains were quickly removed. The vaccine of example 4 was evaluated in rats to determine its effect on the distribution of nicotine in plasma and brain.

A. Active Immunization

Figure 1:
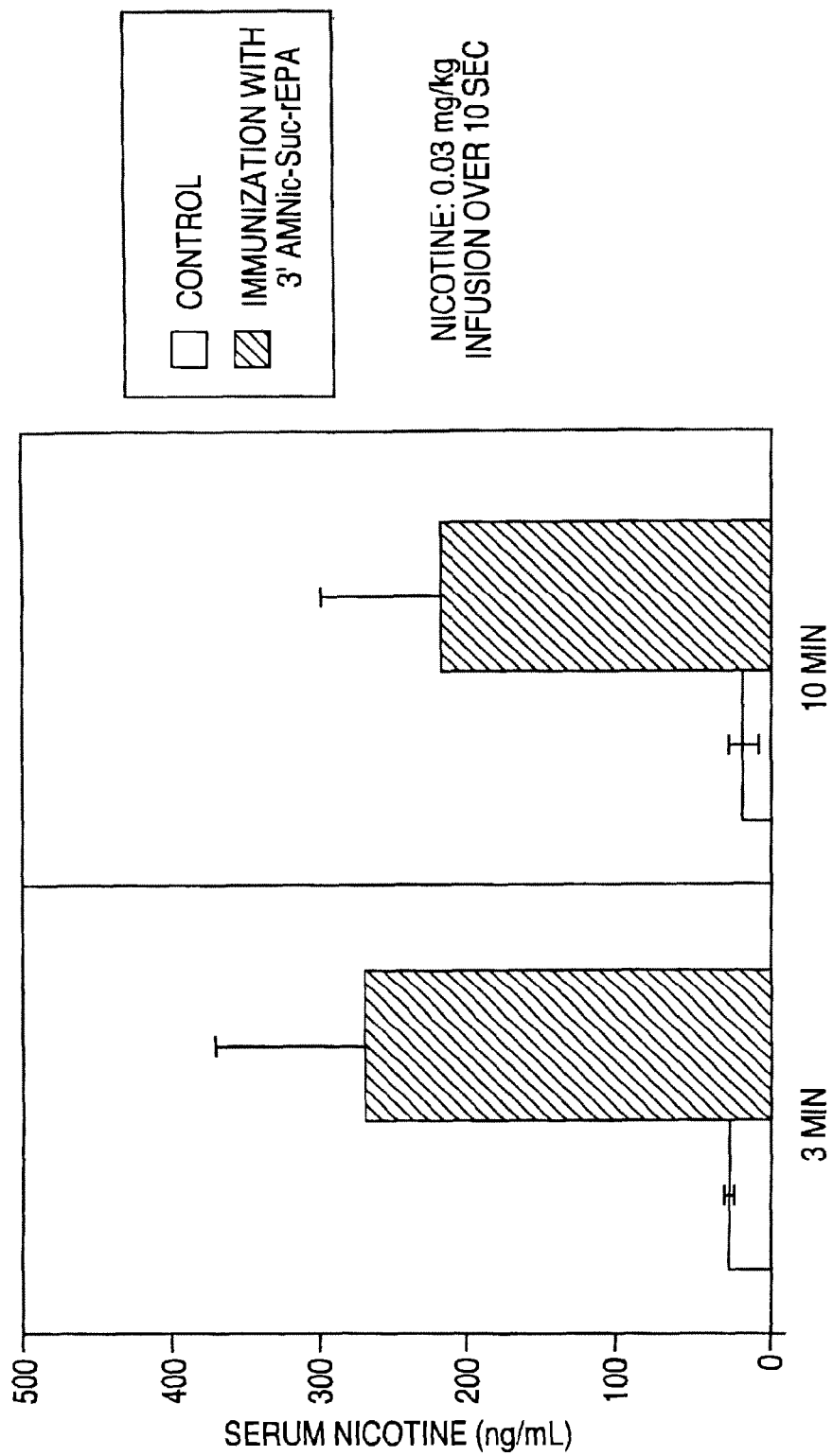
FIG. 1 is a chart that shows the effect of active immunization, with a 3'AMNic-Suc-rEPA conjugate vaccine, on nicotine blood serum levels in rats, following a singe injection of nicotine. Nicotine serum levels, 3 and 10 minutes after nicotine injection, are shown.

Rats were immunized with the nicotine vaccine by three i.p. injections of 25 μg total per injection of vaccine (3'AMNic-Suc-rEPA) two weeks apart. These animals had increased levels of nicotine in plasma 3 and 10 min after an infusion of 0.03 mg/kg of nicotine over 10 seconds, compared with levels in non-immunized controls. See FIG. 1. Thus, active immunization was effective in increasing nicotine binding in plasma. It is known that a modest reduction in the amount of nicotine reaching the brain can dramatically alter the behavioral effects of nicotine.

B. Passive Immunization

Figure 2:
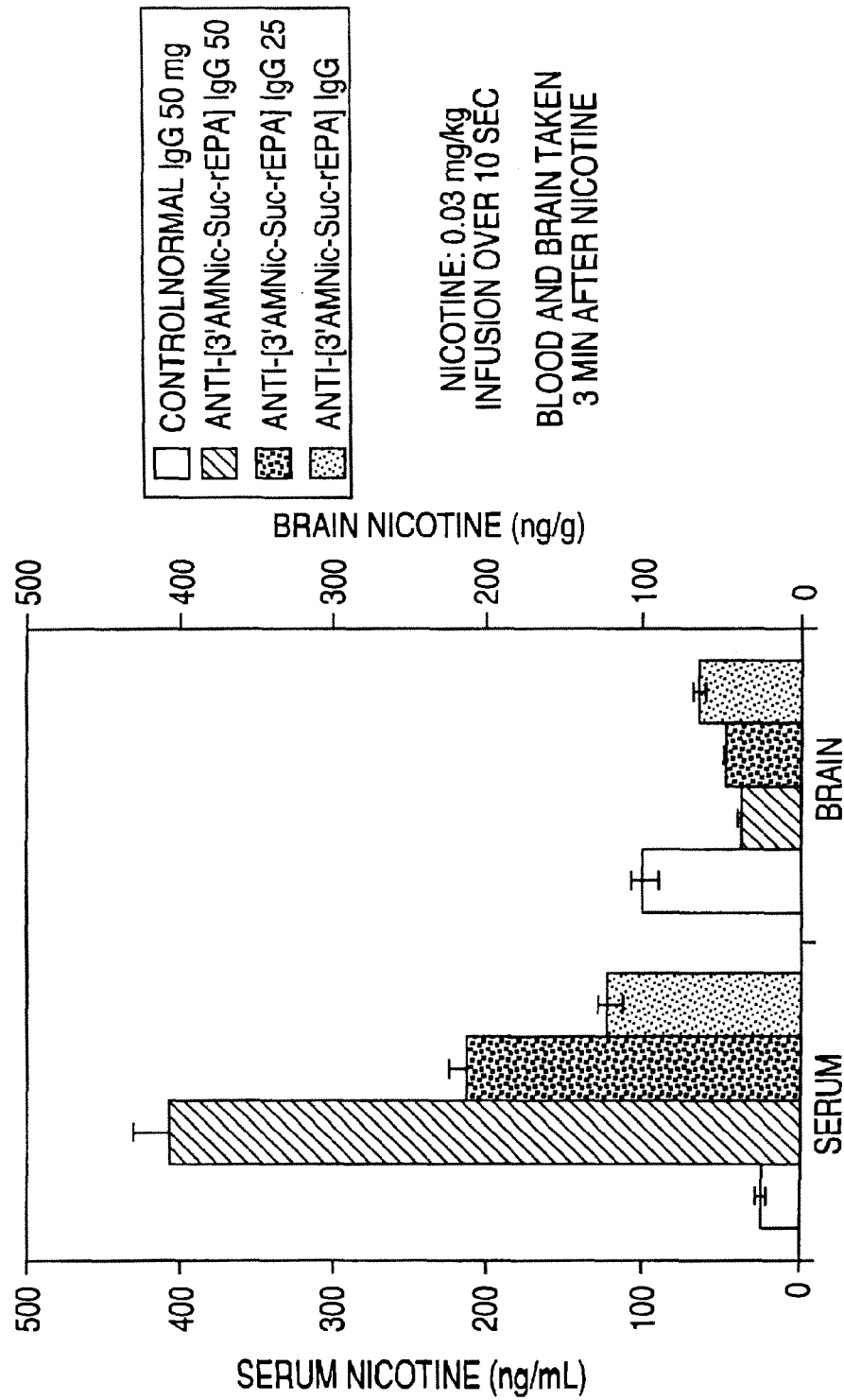
FIG. 2 shows the effect of passive immunization, with antibodies against 3'-AMNic-Suc-rEPA, on nicotine levels in blood and brain of rats. Rats were treated with 12.5, 25 and 50 mg of antibody.

With passive immunization, it was possible to determine the dose response effect of immune IgG in increasing plasma nicotine levels and reducing brain nicotine levels. Rats were administered with varying amounts of anti-(3'AMNic-Suc-rEPA) IgG (12.5 to 50 mg) total per injection. As shown in FIG. 2, there was a clear dose response effect—increasing the dose of IgG increased serum nicotine and decreased brain nicotine levels.

Figure 3:
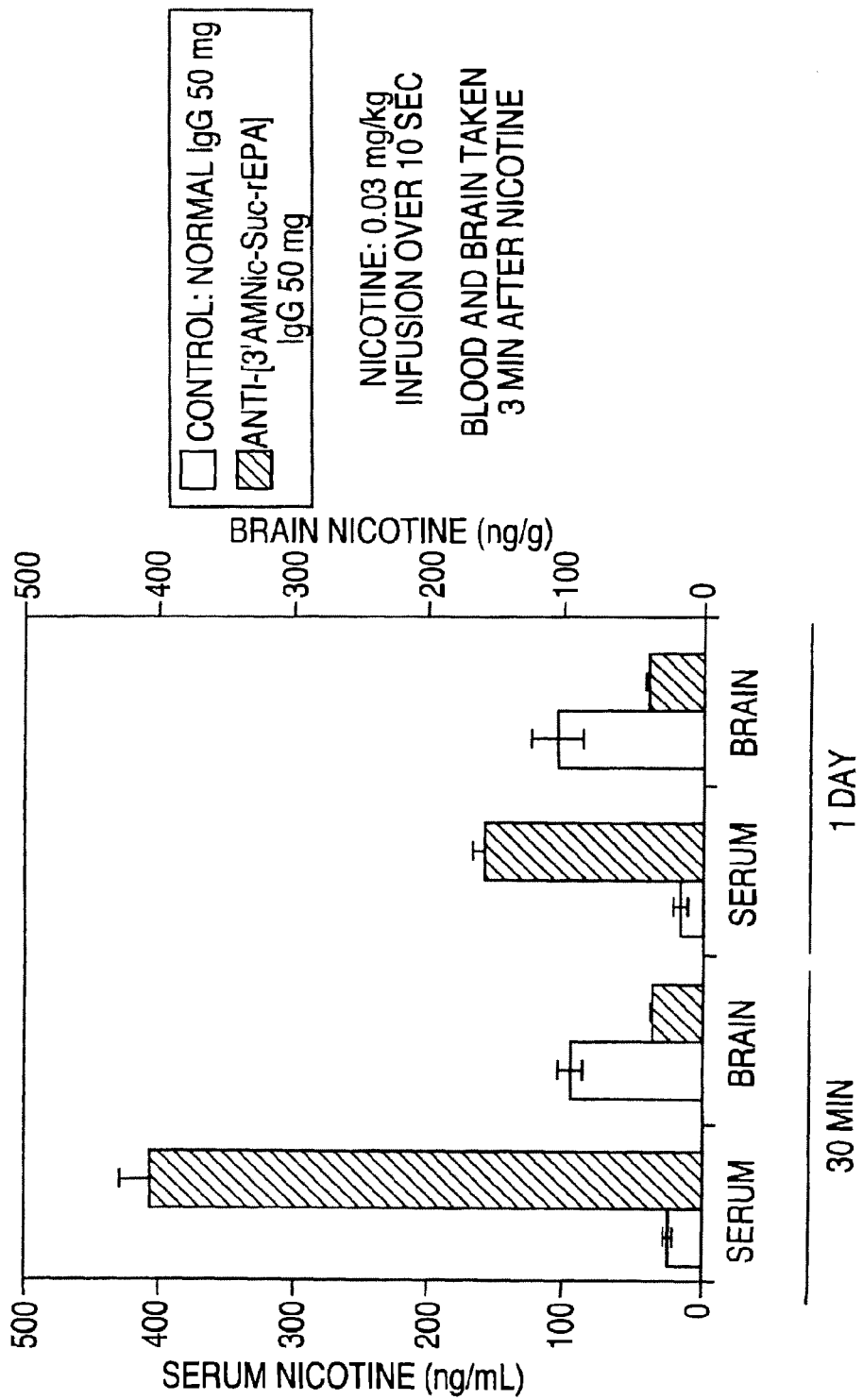
FIG. 3 shows the effects of passive immunization, with antibodies against 3'-AMNic-Suc-rEPA, on nicotine levels in blood serum and brain, in rats. Nicotine levels were measured 30 minutes and 1 day after antibody administration and 3 minutes for nicotine injection.

FIG. 3 shows that anti-nicotine antibodies (anti-3'AMNic-Suc-rEPA) were present and active in the serum of rats, 30 min and 1 day after administration of antibodies (50 mg) total per injection. FIG. 3 shows that following nicotine challenge (0.03 mg/kg infusion over 10 seconds), these antibodies were effective in reducing nicotine concentrations in brain and increasing nicotine levels in plasma, at 30 minutes and 1 day after antibody administration.

Another demonstration of the efficacy of the passive immunization with nicotine vaccine of the invention is its ability to combat consecutive infusions of nicotine. In a separate passive immunization experiments in rats, multiple doses of nicotine did not deplete the antibodies present or significantly reduce their capacity to bind to freshly injected nicotine. In FIG. 4, 50 mg of anti-[3'AMNic-Suc-rEPA] was infused at time zero. 24 hours later, five nicotine injections were made—0.03 mg/kg nicotine was infused over 10 seconds, from the right jugular vein, every 20 minutes for 80 minutes. A total of five nicotine injections were made. The fifth injection of nicotine was spiked with $^3$H-nicotine. Total blood and brain were collected 1 minute after the fifth injection. The results are shown below, and are graphically represented in FIGS. 4 and 5

| | Nicotine Concentrations (mean ± SD) | | | | | |
|---|---|---|---|---|---|---|
| | Serum (ng/mL) | | | | Brain (ng/g) | |
| | 1st dose | 5th dose | | | 5th dose | |
| | Nicotine | Nicotine | 3H-Nicotine | Cotinine | Nicotine | 3H-Nicotine |
| Immune IgG | 245 ± 30 | 343 ± 46 | 121 ± 17 | 30 ± 4 | 244 ± 33 | 90 ± 16 |
| Control IgG | 21 ± 3 | 55 ± 9 | 41 ± 4 | 35 ± 5 | 257 ± 29 | 126 ± 14 |
| % change | +1067 | +524 | +195 | −17 | −13 | −29 |

These results show that even after the fifth dose of nicotine, the antibodies are effective in increasing serum nicotine levels, and decreasing brain nicotine levels. The results with the $^3$H-nicotine demonstrate that antibodies are effective against the nicotine injected at the fifth dose.

Example 13

Evaluation of Locomotor Effects of Nicotine

This experiment used was designed to determine whether passive immunization could prevent an immediate CNS mediated action of nicotine. The rat model used in this experiment was developed by Dr. David Malin and is described in Malin et al. *Nicotine-speafic IgG reduced distribution to brain and attenuates its behavioral and cardiovascular effects in rats*, submitted to the Fifth Annual Meeting of the Society for Research on Nicotine and Tobacco, San Diego, Calif., Mar. 5-7, 1999: To establish a baseline, the effect of a subcutaneous injection of 0.8 mg/kg of nicotine tartrate on locomotor activity level of rats was measured. The 0.8 mg/kg dose of nicotine tartrate is the highest dose that could be used without inducing locomotor abnormalities.

There was an increase in activity level after nicotine injection in rats that were not pre-treated with anti-[3'AMNic-Suc-rEPA], and in rats that were pretreated with 50 mg of normal rabbit serum IgG. See FIG. 6A, right bar and FIG. 6B, left bar. This effect was suppressed by pretreating the Animals with 50 mg of anti-[3'AMNic-Suc-rEPA] immune IgG (FIG. 6B, right bar). This shows that the anti-nicotine antiserum eliminated a stimulant effect of nicotine, in vivo.

Example 14

Evaluation of Nicotine on Systolic Blood Pressure

In this experiment, another indicator of the behavioral effect of nicotine was measured: the change in systolic blood pressure. Rats were pretreated with anti-[3'AMNic-Suc-rEPA] IgG, or control IgG. Rats were treated with a subcutaneous injection of 0.1 mg/kg nicotine tartrate. Control rats showed an increase in systolic blood pressure of 42.6±3.2 mm Hg, when treated with nicotine. When rats were pretreated with anti-nicotine antiserum IgG, the nicotine challenge was less effective. When increasing amounts of anti-nicotine serum were administered, this diminished the ability of nicotine to raise blood pressure. As shown in FIG. 7, there was a negative linear trend of blood pressure as a function of IgG dose.

What is claimed is:

1. A method of treating or preventing nicotine addiction in a patient in need thereof, comprising administering a therapeutically effective amount of a hapten of formula II:

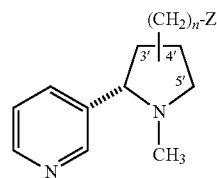

(II)

wherein
n is 1 to 12;
Z is NH$_2$, COOH, CHO or SH, and
—(CH$_2$)$_n$—Z is bonded to the 3', 4' or 5' position, wherein the Z moiety is bound to a carrier protein, directly or via a linker,
further comprising administering another compound that is useful in the treatment of addiction.

2. The method of claim 1, wherein the other compound is an anti-depressant drug.

3. The method of claim 2, wherein the anti-depressant drug is selected from the group consisting of bupropion and fluoxetine.

* * * * *